US012167255B2

(12) United States Patent
Lin et al.

(10) Patent No.: US 12,167,255 B2
(45) Date of Patent: Dec. 10, 2024

(54) NON-RECOMBINANT HUMAN INSULIN-LIKE GROWTH FACTOR BINDING PROTEIN CONCENTRATE

(71) Applicant: Siemens Healthcare Diagnostics Inc., Tarrytown, NY (US)

(72) Inventors: Spencer Lin, Walnut Creek, CA (US); Kwasi Osae-Kwapong, White Plains, NY (US); Omar Quraishi, Maplewood, NJ (US); Seema Sinha, Rancho Santa Margarita, CA (US); Michele Smith, Poughkeepsie, NY (US); SunRay DiFrancesco, Peekskill, NY (US); Ryan Spears, Stamford, CT (US); Dharini Rawal, Washington Township, NJ (US); Debra Hovanec-Burns, Wappingers Falls, NY (US); Robert Owens, Danbury, CT (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 656 days.

(21) Appl. No.: 16/949,817

(22) Filed: Nov. 16, 2020

(65) Prior Publication Data
US 2021/0072266 A1 Mar. 11, 2021

Related U.S. Application Data

(62) Division of application No. 16/067,589, filed as application No. PCT/US2016/068901 on Dec. 28, 2016, now abandoned.

(60) Provisional application No. 62/274,116, filed on Dec. 31, 2015.

(51) Int. Cl.
| | |
|---|---|
| *H04W 24/02* | (2009.01) |
| *A61K 38/00* | (2006.01) |
| *A61K 38/17* | (2006.01) |
| *C07K 14/435* | (2006.01) |
| *C07K 14/47* | (2006.01) |
| *G01N 33/96* | (2006.01) |
| *H04B 7/06* | (2006.01) |
| *H04L 41/0806* | (2022.01) |
| *H04W 8/00* | (2009.01) |
| *H04W 72/044* | (2023.01) |
| *H04W 84/18* | (2009.01) |

(52) U.S. Cl.
CPC ......... *H04W 24/02* (2013.01); *A61K 38/1754* (2013.01); *C07K 14/435* (2013.01); *C07K 14/4743* (2013.01); *G01N 33/96* (2013.01); *H04B 7/0617* (2013.01); *H04L 41/0806* (2013.01); *H04W 8/005* (2013.01); *H04W 72/046* (2013.01); *A61K 38/00* (2013.01); *H04W 84/18* (2013.01)

(58) Field of Classification Search
None
See application file for complete search history.

(56) References Cited

U.S. PATENT DOCUMENTS

| | | | |
|---|---|---|---|
| 5,187,151 | A | 2/1993 | Clark et al. |
| 5,955,128 | A | 9/1999 | Bayevsky et al. |
| 6,066,464 | A | 5/2000 | Khosravi et al. |
| 6,248,546 | B1 | 6/2001 | Khosravi et al. |
| 2011/0045510 | A1 | 2/2011 | Lang et al. |

FOREIGN PATENT DOCUMENTS

| | | |
|---|---|---|
| CN | 1315868 | 10/2001 |
| JP | H06501270 | 2/1994 |
| JP | H06505235 | 6/1994 |
| WO | 9218154 | 10/1992 |
| WO | 1994046597 | 9/1999 |
| WO | 2014089262 | 6/2014 |

OTHER PUBLICATIONS

Ritchie et al. (Labome; Protein Purification Nov. 17, 2012).*
LaBreck et al. ("An economical analysis of single use tangential flow filtration for biopharmaceutical application" Nov. 2, 2010 BioPharm International vol. 2010, supplement, Issue 9).*
Clemmons ("Insulin-like Growth Factor Binding Proteins and their role in controlling IGF actions" Cytokine and Growth Factor Reviews vol. 8, No., 1, pp. 45-62, 1997).*
Wen J. et al: "Automated Chemiluminescent Immunoassays of Insulin-Like Growth Factor I and Insulin-Like Growth Factor Binding Protein 3 on the Immulite Analyzer"; DPC Scientific Poster D-50 American Association for Clinical Chemistry (AACC) 54th Annual Meeting and Clinical Lab Exposition Jul. 28-Aug.; Clin Chem; 1-15; XP055522234, Retrieved from the Internet: URL:http://www.dpcweb.com/documents/posters/aacc02/ZA040.pdf [retrieved on Nov. 8, 2018] / Jan. 1, 2002.
(Leal, et al.) The Type V Transforming Growth Factor b Receptor Is the Putative Insulin-like 1-7 ., Growth Factor-binding Protein 3 Receptor. The Journal of Biological Chemistry. 1997, vol. 272, pp. 20572-20576, doi: 10.1074/ibc.272.33.20572; abstract; Figure 1A; p. 20573, first column, sixth paragraph.
(Biolegend) Product Data Sheet: Recombinant Human IGFBP-3 (Carrier Free). Sep. 19, 2014; p. 1, second-third and ninth paragraphs.
(Mediagnost) IGFBP-3 ELISA: Enzyme-Immunoassay for Quantitative Determination of_.-Insulin-Like-Growth-Factor Binding Protein-3. May 4, 2006, pp. 1-25; p. 7, second paragraph; p. 10, fourth paragraph; p. 11, third-fourth paragraphs; p. 16, second paragraph; p. 17, fourth paragraph.
(Beckman Coulter) Active IGFBP-3 IRMA. Directions for Use. Jan. 1, 2010; p. 1, 8-11 . first column, second paragraph; p. 1, first column; fifth paragraph; p. 2, first column, first paragraph.

(Continued)

*Primary Examiner* — James H Alstrum-Acevedo
*Assistant Examiner* — Tara L Martinez

(57) ABSTRACT

A human insulin-like growth factor (IGF) binding protein stock solution and method of making the same include a non-recombinant human IGF binding protein-3 (nr-IGFBP-3) in an aqueous buffered medium. The concentration of the nr-IGFBP-3 in the stock solution ranges from about 16 micrograms per milliliter (μg/ml) to about 40 μg/ml. A kit includes a set of calibrators for nr-IGFBP-3. The set of calibrators includes the nr-IGFBP-3 in different concentrations.

21 Claims, 5 Drawing Sheets

(56) References Cited

OTHER PUBLICATIONS

PCT Search Report and Written Opinion mailed on Mar. 16, 2017 for International Application No. PCT/US16/68901, 8 pp.

Sigma Aldrich; "Buffer reference center"; (<https://www.sigmaaldrich.com/life-science/core-bioreagents/biological-buffers/learning-center/buffer-reference-center.html> available Oct. 26, 2008).

Sigma Aldrich; "Phosphate buffer solution"; (<https://www.sigmaaldrich.com/catalog/product/sigma/1805?lang=en&region=US&gclid=EAlalQobChMl7aa9jerF6wlVQQilCR1lEw7VEAAYAyAAEgK-YfD_BwE> accessed Aug. 31, 2020.

"WHO International Biological Reference Preparations Held and Distributed by the WHO International Laboratories for Biological Standards Endocrinological Substances", Feb. 8, 2013, p. 1-4, (https://www.who.int/bloodproducts/catalogue/EndoFeb2013.pdf.

"WHO International Standard 1st WHO International Standard for Insulin-like Growth Factor-1, recombinant, human, for immunoassay NIBSC code: 02/0254 Instructions for use" Jun. 4, 2013, (https://www.nibsc.org/documents/ifu/02-254.pdf).

Michael B. RFanke, Best Practice & Research Clinical Endocrinology & Metabolism, Insulin-like growth factor binding-protein-3(IGBP-3) (Oct. 2015) 29(5):701-711.

"Non WHO Reference Material Insulin-Like Growth Factor Binding Protein-3 NIBSC code: 93/560 Instructions for use", Jan. 21, 2008, (cf. https:/www.nibsc.org/documents/ifu/93-560.pdf).

Cambridge Dictionary "patient"; Patient Definition in the English Dictionary; pp. 1-6; https ://dictionary.cambridge .org/us/dictionary/english/patient / Feb. 23, 2020.

IGF-I Package Insert—Immulite 2000 System.

IGFBP-3 Package Insert—Immulite 2000 System.

GE Healthcare Instructions 71-5002-39 AC_Phenyl Sepharose 6 Fast Flow.

Bauchat et al, Journal of Endocrinology, Biochemical and functional analysis of a conserved IGF-binding protein isolated from rainbow trout hepatoma cells; v. 170, 619-628; (2001).

Baxter, R C et al., Journal of Biological Chemistry, High molecular weight insulin-like growth factor binding protein complex, vol. 264, Issue 20, 11843-11848, (1989).

Jinglian, Zhao : "New technology to generate prosperity with science and technology—50 cases of practical biochemical products manufacturing"; Dec. 31, 1993.

* cited by examiner

NON-RECOMBINANT HUMAN INSULIN-LIKE GROWTH FACTOR BINDING PROTEIN CONCENTRATE

CROSS-REFERENCE TO RELATED APPLICATIONS/INCORPORATION BY REFERENCE STATEMENT

This application is a divisional of U.S. Ser. No. 16/067,589, filed Jun. 29, 2018; which is a US national stage application filed under 35 USC § 371 of International Application No. PCT/US2016/068901, filed Dec. 28, 2016; which claims priority to U.S. Ser. No. 62/274,116, filed Dec. 31, 2015. The entire contents of the above-referenced patents/patent applications are hereby expressly incorporated herein by reference.

STATEMENT REGARDING FEDERALLY SPONSORED RESEARCH OR DEVELOPMENT

Not applicable.

BACKGROUND

Insulin-like growth factors (IGF), for example, IGF-1 and IGF-2, belong to a family of protein hormones involved in the regulation of cell growth. The liver secrets the IGF-1, for example, as a result of growth hormone (GH) stimulation. The actions of IGF are mediated by binding to insulin-like growth hormone binding proteins (IGFBP). There are six IGF binding proteins with high affinity for IGF-1 and IGF-2 (e.g., IGFBP-1 to IGFBP-6) with IGFBP-3 being the most predominant. The IGFBP facilitate modulation of the action of IGF in order to one or both of inhibit IGF action in some situations and promote IGF action in other situations. In particular, IGF-1 binds to IGFBP-3 in a 1:1 molar ratio. It appears that production of IGFBP-3, as well as IGF-1, is dependent on growth hormone GH, while in contrast, IGFBP-1 production is regulated by the peptide hormone insulin.

IGFBP-3 transports IGF, e.g., either IGF-1 or IGF-2, and an acid-labile subunit (ALS) protein (also GH dependent) in stable complexes of IGFBP-3 in the bloodstream to tissues of the body, and IGFBP-3 has circulatory, extracellular and intracellular functions. For example, IGFBP-3 can bind IGF from various cell types; can block access of IGF to IGF receptors; can interact with proteins at a cell surface; and can bind to hormone receptors in a cell nucleus.

IGF levels in the human body are monitored for the purpose of characterization of health and diseases. For example, IGF-1, similar in structure to insulin, plays an important role in childhood growth. Monitoring the levels of IGF during childhood development facilitates characterizing whether development is normal. In other examples, the IGF play important roles in monitoring diabetes, and possibly aging and cancer. Therefore, monitoring levels of IGF, in particular IGFBP-3 levels, in humans via blood serum immunoassays provides important diagnostic tools for monitoring both children and adults.

Results from immunoassays of patient samples of human blood serum for IGFBP-3 levels are compared to a set of calibrators or standards of known IGFBP-3 concentration. For example, IGFBP-3 calibration standards are prepared at a variety of concentrations spanning a suspected concentration range of interest of an IGFBP-3 analyte expected in patient samples. The calibrators are used to calibrate immunoassay equipment including, but not limited to, IMMU-LITE® systems and CENTAUR® systems, for example, both from Siemens Healthcare Diagnostics, Inc., so that IGFBP-3 analyte levels in human patients can be measured with accuracy.

While IGFBP-3 is relatively abundant in human blood serum, isolating IGFBP-3 from human blood in sufficient concentration in order to prepare sets of calibration standards for immunoassays has been found to be problematic and difficult. Instead, recombinant forms of human IGFBP-3 have been used in preparing calibration standards for immunoassays of patient samples.

Unfortunately, commercially available recombinant forms of human IGFBP-3 are expensive and may not have structural integrity that a purely human form of IGFBP-3 has. Therefore, the negative impact of using recombinant forms of human IGFBP-3 in immunoassay calibration standards may be more significant than just a cost concern.

BRIEF DESCRIPTION OF THE DRAWINGS

Various features of embodiments and examples in accordance with the principles described herein may be more readily understood with reference to the following detailed description taken in conjunction with the accompanying drawings, where like reference numerals designate like structural elements, and in which.

Figure 1A:
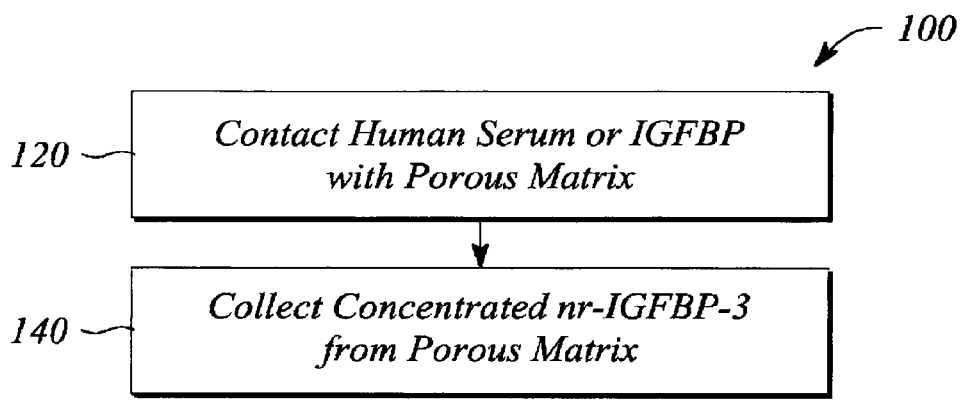
FIG. 1A illustrates a flow chart of a method of forming a concentrate of a non-recombinant human insulin-like growth factor (IGF) binding protein 3 (nr-IGFBP-3) in aqueous solution in an example, according to an embodiment consistent with the principles described herein.

Certain examples and embodiments have other features that are one or both of in addition to and in lieu of the features illustrated in the above-referenced figures. These and other features are detailed below with reference to the above-referenced figures.

DETAILED DESCRIPTION

In some embodiments in accordance with the principles described herein, a human insulin-like growth factor (IGF) binding protein stock solution is provided. The human insulin-like growth factor (IGF) binding protein stock solution comprises a non-recombinant human IGF binding protein-3 (nr-IGFBP-3) in an aqueous buffered medium having an nr-IGFBP-3 concentration ranging from about 16 micrograms per milliliter (μg/ml) to about 40 μg/ml.

In some embodiments in accordance with the principles described herein, a kit comprising a set of calibration standards for human insulin-like growth factor (IGF) binding protein is provided. Each calibration standard of the set comprises an aqueous solution that comprises a non-recombinant human IGF binding protein 3 (nr-IGFBP-3). A concentration of the nr-IGFBP-3 in each calibration standard of the set is different, and the different concentrations of the nr-IGFBP-3 in the set are within a range of from about 0.5 μg/ml to about 16 μg/ml.

In some embodiments in accordance with the principles described herein, a method of forming a concentrate of a non-recombinant human insulin-like growth factor (IGF) binding protein 3 (nr-IGFBP-3) in aqueous solution is provided. The method comprises contacting an aqueous solution of one of human serum and IGF binding protein from the human serum with a porous matrix and, after contacting the porous matrix, collecting concentrated nr-IGFBP-3 in aqueous solution, wherein the collected nr-IGFBP-3 in aqueous solution has a concentration within a range of from about 16 μg/ml to about 40 μg/ml.

Embodiments and examples consistent with the principles described herein provide a stock solution of human insulin-like growth factor (IGF) binding protein comprising a concentrate of non-recombinant form of human IGF binding protein-3 (nr-IGFBP-3) in an aqueous medium. The nr-IGFBP-3 concentrate in the stock solution is in a concentration sufficient to prepare a set of calibration standards for immunoassays of IGFBP-3 analyte patient samples. The phrase 'concentration sufficient to prepare a set of calibration standards' means that the concentration of nr-IGFBP-3 in the stock solution is at least as high as the highest concentration of an nr-IGFBP-3 calibration standard ('calibrator') for a particular assay.

Embodiments and examples consistent with the principles described herein further provide a set of calibration standards that comprises different concentrations of nr-IGFBP-3 configured to span a suspected concentration range of interest of an IGFBP-3 analyte expected in patient samples. In some examples, the IGFBP-3 analyte levels in human patient samples may range from as little as about 0.5 μg/ml, where a limit of quantification (LOQ) in an assay is less than about 0.1 μg/ml, to as much as about 16 μg/ml. However, human serum typically has a range of about 4.0 μg/ml to about 5.5 μg/ml of nr-IGFBP-3, which is an insufficient concentration to make calibration standards to span a suspected range in human patients. In accordance with the principles described herein, the IGF binding protein stock solution has an nr-IGFBP-3 concentration ranging of from about 16 μg/ml to about 40 μg/ml.

Moreover, the set of calibration standards that spans the suspected concentration range of patient sample IGFBP-3 analyte is prepared from the IGF binding protein stock solution. The calibration standards of the set have different concentrations of the nr-IGFBP-3 that range from about 0.5 μg/ml to about 16 μg/ml. The IGF binding protein stock solution is made by a method of forming a concentrate of nr-IGFBP-3 in aqueous solution. The method comprises contacting an aqueous solution of human serum or IGF binding protein from the human serum with a porous matrix and collecting concentrated nr-IGFBP-3 in aqueous solution from the porous matrix, wherein the nr-IGFBP-3 in the concentrated aqueous solution has a concentration within a range of from about 16 μg/ml to about 40 μg/ml. Contacting the aqueous solution of human serum or IGF binding protein from the human serum with the porous matrix is configured to both perform a buffer exchange and concentrate the nr-IGFBP-3 solution. In some examples of the method, contacting the aqueous solution further provides one or more of separating nr-IGFBP-3 or IGF binding protein from other serum proteins in solution, desalting the nr-IGFBP-3 or IGF binding protein solution, purifying and enriching the nr-IGFBP-3 solution.

The concentrated nr-IGFBP-3 in the stock solution is in a native heterogeneous form that is the same as is found in human patients. By 'native heterogeneous form' it is meant that the nr-IGFBP-3 from human serum is glycosylated and may have several forms including that the nr-IGFBP-3 may form one or more of a binary complex with IGF-1, IGF-2 or ALS, a ternary complex with IGF-1 or IGF-2 and ALS, and may not form a complex with any of these. According to the principles described herein, all these forms representing a native heterogeneous form of nr-IGFBP-3 are as is also found in endogenous human serum. The nominal molecular weight of the native heterogeneous form of nr-IGFBP-3 may range from about 25 kilo Daltons (kDa) to about 155 kDa, for example.

Recombinant forms of IGFBP-3 are structurally different from the nr-IGFBP-3 from human blood in non-trivial ways. Owing to the structural differences of recombinant IGFBP-3 forms, a significant bias in dose recovery may be observed when using recombinant sources of IGFBP-3 as compared to endogenous human sources, both at ambient temperature and under varying temperature ranges for a common laboratory. By definition herein, the 'recombinant IGFBP-3' is neither bound to an insulin-like growth factor (e.g., IGF-1 or IGF-2) nor bound to an acid labile subunit (ALS). Moreover, the recombinant forms of IGFBP-3 lack glycosylation found in nr-IGFBP-3 in human blood. The recombinant IGFBP-3 is substantially a 'naked' form. The nr-IGFBP-3 from human blood is a native heterogeneous form, as described above, that mimics the IGFBP-3 in human patients, because nr-IGFBP-3 may include each of bound IGF, ALS and glycosylation units in a ternary complex of about 150 kDa, or may form a binary complex with bound IGF or ALS, or may not be complexed with either IGF or ALS.

The present inventors have discovered that recombinant IGFBP-3 forms have a temperature bias in a range of ambient temperatures (i.e., about 18 degrees Celsius (° C.) to about 30° C.) typically associated with immunoassay temperature conditions, which may be detrimental to immunoassay accuracy, as is further provided in the Examples section below. The phrase 'ambient temperature bias' means that the measured concentration of recombinant IGFBP-3 in a sample may be different depending on the temperature of the laboratory at which the measurement is made.

For example, a sample of recombinant IGFBP-3 may be measured to be 3 µg/ml at 24° C. (i.e., ambient temperature). However, if the temperature of the environment in which the recombinant IGFBP-3 is used or measured is changed to below or above about 24° C. (e.g., about 18° C. or about 30° C.), the concentration of the same recombinant IGFBP-3 sample also changes to be greater than or less than the ambient-measured 3 µg/ml at 24° C. The nr-IGFBP-3 from human blood, as well as the IGFBP-3 analyte in human patient samples, does not have this temperature bias. As such, the observed temperature bias of recombinant IGFBP-3 is significant when considering immunoassays and calibration standards. The accuracy of immunoassay measurements of IGFBP-3 analyte levels in human patient samples is dependent on the accuracy of the calibration standards and controls used in the immunoassay in the temperature range that the immunoassay is performed.

Moreover, as used herein, 'Medical Decision Pool' or ('MDP') is broadly defined as a set of calibration standards having a low (or lowest) concentration range of an analyte suspected to be measured in patient samples. 'Limitation of Quantification' ('LOQ') is broadly defined as the lowest concentration of an analyte suspected to be found in a patient sample that can be measured reliably. For example, the LOQ of IGFBP-3 analyte concentration in patient samples is about equal to or less than 0.1 µg/ml.

Further, as used herein, the article 'a' is intended to have its ordinary meaning in the patent arts, namely 'one or more'. For example, 'a protein' means one or more proteins and as such, 'the protein' means 'the protein(s)' herein. Also, any reference herein to 'top', 'bottom', 'upper', 'lower', 'up', 'down', 'front', back', 'first', 'second', 'left' or 'right' is not intended to be a limitation herein. Herein, the term 'about' when applied to a value generally means within the tolerance range of the equipment used to produce the value, or may mean plus or minus 10%, or plus or minus 5%, or plus or minus 1%, or a range between any of these percent values, unless otherwise expressly specified. Further, herein the term 'substantially' as used herein means a majority, or almost all, or all, or an amount within a range of about 51% to about 100%. Moreover, examples herein are intended to be illustrative only and are presented for discussion purposes and not by way of limitation.

Human IGF Binding Protein Stock Solution

In accordance with some embodiments of the principles described herein, a human IGF binding protein stock solution is provided that comprises nr-IGFBP-3 from human blood in an aqueous buffered medium. The IGF binding protein stock solution has a concentration of nr-IGFBP-3 that is sufficient to prepare a set of calibration standards for an immunoassay of IGFBP-3 analyte in patient samples. In particular, the concentration of nr-IGFBP-3 in the IGF binding protein stock solution is sufficient to prepare a set of calibration standards that span a suspected range of IGFBP-3 analyte levels in human patient samples. In some examples, the IGF binding protein stock solution has a concentration of nr-IGFBP-3 that is within a range of from about 16 µg/ml to about 40 µg/ml. It should be understood that the nr-IGFBP-3 is in native heterogeneous form, as described above, and therefore, there may be a certain percentage of the total nr-IGFBP-3 bound to either IGF-1 or IGF-2, for example, in a 1:1 complex, in the stock solution.

In some examples, the nr-IGFBP-3 concentration in the IGF binding protein stock solution is within the range of from about 16 µg/ml to about 38 µg/ml, or from about 16 µg/ml to about 36 µg/ml, or from about 16 µg/ml to about 34 µg/ml, or from about 16 µg/ml to about 32 µg/ml, or from about 16 µg/ml to about 30 µg/ml. In some examples, the nr-IGFBP-3 concentration in the IGF binding protein stock solution is within the range of from about 18 µg/ml to about 40 µg/ml, or from about 20 µg/ml to about 40 µg/ml, or from about 22 µg/ml to about 40 µg/ml, or from about 24 µg/ml to about 40 µg/ml, or from about 26 µg/ml to about 40 µg/ml, or from about 28 µg/ml to about 40 µg/ml, or from about 30 µg/ml to about 40 µg/ml. In some examples, the nr-IGFBP-3 concentration in the IGF binding protein stock solution is within the range of from about 20 µg/ml to about 36 µg/ml, or from about 20 µg/ml to about 30 µg/ml, or is greater than 20 µg/ml and less than 40 µg/ml. In some examples, the nr-IGFBP-3 concentration in the IGF binding protein stock solution is equal to about 25 µg/ml, or about 35 µg/ml. In an example, the nr-IGFBP-3 concentration in the IGF binding protein stock solution is equal to about 30 µg/ml.

As mentioned above, the nr-IGFPB-3 concentration in the IGF binding protein stock solution is sufficient to prepare a set of calibration standards, which include calibration standards having different nr-IGFPB-3 concentrations, wherein the calibration standards of the set include a range of nr-IGFBP-3 concentrations that spans a suspected concentration range of the IGFBP-3 analyte in patient samples. In particular, the set of calibrations standards comprises the IGF binding protein stock solution diluted with an aqueous medium such as, but not limited to, an aqueous buffered medium, human serum, or a combination or mixture thereof, for example. The dilutions of the IGF binding protein stock solution are configured to provide the different concentrations of nr-IGFBP-3 in each calibration standard of the set. In some examples, the different nr-IGFBP-3 concentrations of the calibration standards in the set range from about 0.5 µg/ml to about 16 µg/ml. The set of calibration standards is described further below.

According to the various embodiments herein, the IGF binding protein stock solution is made from human blood serum, and the aqueous buffered medium of the nr-IGFBP-3 in the IGF binding protein stock solution is derived from the human blood serum. In some examples, one or both of the IGF binding protein stock solution and the aqueous buffered medium of nr-IGFBP-3 is exclusive of recombinant IGF binding protein. The phrase 'exclusive of recombinant IGF binding proteins' means that the stock solution or the aqueous buffered medium comprises no recombinant IGF binding protein, or for example, about 0% of recombinant IGF binding protein. In some examples, a recombinant IGFBP-3 reference control may be included in a kit that comprises the set of calibration standards, for example. Recombinant IGFBP-3 reference controls, which may be a non-World Health Organization (WHO) material, may be obtained from the National Institute for Biological Standards and Control (NIBSC) in the United Kingdom.

A Set of nr-IGFBP-3 Calibration Standards and a Kit Comprising Same

In accordance with some embodiments of the principles described herein, a kit comprising a set of calibrators (e.g., calibration standards or controls) for immunoassays of human patient IGFBP-3 analyte levels is provided. A calibrator of the set is an aqueous solution that comprises nr-IGFBP-3 in a concentration that is different from concentrations of nr-IGFBP-3 in other calibrators in the set. The different concentrations of the calibrators in the set are configured to span a suspected concentration range of an IGFBP-3 analyte in the patient samples.

In some examples, the different nr-IGFBP-3 concentrations of the calibrators in the set range from about 0.25 µg/ml to about 18.50 µg/ml to span a suspected concentration range of the IGFBP-3 analyte in patient samples. In some examples, the different nr-IGFBP-3 concentrations of the calibrators in the set range from about 0.35 µg/ml to about 18.50 µg/ml, or from about 0.45 µg/ml to about 18.50 µg/ml, or from about 0.55 µg/ml to about 18.50 µg/ml, or from about 0.65 µg/ml to about 18.50 µg/ml, or from about 0.75 µg/ml to about 18.50 µg/ml, to span a suspected concentration range of the IGFBP-3 analyte in patient samples. In some examples, the different nr-IGFBP-3 concentrations of the calibrators in the set range from about 0.50 µg/ml to about 17.50 µg/ml, or from about 0.50 µg/ml to about 16.50 µg/ml, or from about 0.50 µg/ml to about 16.00 µg/ml, or from about 0.50 µg/ml to about 15.50 µg/ml, or from about 0.50 µg/ml to about 15.00 µg/ml, or from about 0.50 µg/ml to about 14.50 µg/ml, or from about 0.50 µg/ml to about 13.50 µg/ml, to span a suspected concentration range of the IGFBP-3 analyte in human patient samples. Moreover, some individual calibrators of the set may represent MDP standards, for example, a calibrator that has an nr-IGFBP-3 concentration of about 0.5 µg/ml, about 3.0 µg/ml or about 6.0 µg/ml may be designated as a MDP standard.

In some examples, the set of calibrators includes different dilutions of a human IGF binding protein stock solution having an nr-IGFBP-3 concentration ranging from about 16 µg/ml to about 40 µg/ml. In some examples, the human IGF binding protein stock solution is substantially similar to the human IGF binding protein stock solution, as described above. The human IGF binding protein stock solution is diluted with a human serum diluent to achieve the range of different concentrations of nr-IGFBP-3 of the set of calibrators that is configured to span a suspected concentration range of IGFBP-3 analyte in immunoassays of patient samples. For example, the set of calibrators may have a range of different concentrations that span from about 0.50 µg/ml to about 16.00 µg/ml, or about 0.50 µg/ml to about 14.50 µg/ml, where about 0.10 µg/ml may be close to LOQ. The phrase 'human serum diluent' refers to a solution that comprises a protein content and concentrations thereof that are as close as possible, or substantially identical, to that found in human serum. For example, MDP standards are made using a human serum diluent solution that is as close to human serum as possible.

The phrase 'aqueous buffered medium' refers to an aqueous medium that may be solely water or may include from 0.1 to about 40 volume percent of a cosolvent such as, for example, a water miscible organic solvent, e.g., an alcohol, an ether or an amide. The pH for the medium will usually be in the range of about 4 to about 11, or in the range of about 5 to about 10, or in the range of about 6.5 to about 9.5, or in the range of about 7.0 to about 9.0, for example. Various buffers may be used to achieve the desired pH and maintain the pH during processing. Illustrative buffers include, but are not limited to, borate, phosphate, carbonate, Tris (i.e., Tris (hydroxymethyl)amino-methane), barbital, PIPES (i.e., piperazine-N,N-bis(2-ethanesulfonic acid)), HEPES (i.e., 4-(2-hydroxyethyl)-1-piperazineethanesulfonic acid), MES (i.e., 2-(N-morpholino)-ethanesulfonic acid), ACES (i.e., N-(2-Acetamido)-2-aminoethanesulfonic acid), MOPS (i.e., 3-(N-morpholino)propanesulfonic acid), BICINE (i.e., N,N-bis(2-hydroxyethyl)-glycine), or a combination or a mixture of two or more of these, for example.

In some examples, a calibrator of the set further comprises a human serum diluent that is substantially free from IGF binding protein to dilute the aqueous solution of nr-IGFBP-3 of that calibrator. In other examples, each of the calibrators of the set further comprises the human serum diluent that is substantially free from IGF binding protein to dilute the aqueous solution of nr-IGFBP-3 to the different nr-IGFBP-3 calibrator concentrations of the set. The phrase 'substantially free from IGF binding protein' means that the human serum diluent has been modified to contain less than about 2% (by volume) IGF binding protein with respect to a starting human serum, or less than about 1.5%, or less than about 1%, or about 0% by volume of IGF binding protein with respect to a starting human serum. For example, a human serum, double charcoal stripped and delipidized, or e.g., DDC MASS SPEC GOLD® Serum, from Golden West Biologicals, Inc., Temecula, CA, may be used as a substantially IGF binding protein-free human serum diluent.

A method of making the human serum diluent that is substantially free from IGF binding proteins is further described below in accordance with an embodiment of the principles described herein. In other examples, the human serum diluent includes IGF binding proteins, and the human serum may be raw plasma or raw serum or processed plasma or processed serum, for example. The human plasma or serum used as the human serum diluent with IGF binding proteins may be obtained from Bioresource Technologies (BRT), Weston, FL, for example.

Further, in some examples, while the immunoassay kit may include a recombinant IGFBP-3 reference control, the calibrators in the set of calibration standards are exclusive of recombinant IGF binding proteins. In other words, the set of calibration standards for determination of levels of nr-IGFBP-3 in patient sample immunoassays includes the nr-IGFBP-3 from only human serum.

A Method of Forming a Concentrate of nr-IGFBP-3 in Aqueous Solution

In accordance with some embodiments of the principles described herein, a method of forming a human IGF binding protein stock solution that comprises a concentrate of nr-IGFBP-3 in aqueous solution is provided. FIG. 1A illustrates a flow chart of a method 100 of forming a concentrate of nr-IGFBP-3 in aqueous solution in an example, in accordance with an embodiment of the principles described herein. The method 100 comprises contacting 120 an aqueous solution of either human serum or IGF binding protein from the human serum with a porous matrix; and collecting 140 concentrated nr-IGFBP-3 in an aqueous solution from the porous matrix. The concentrated nr-IGFBP-3 in aqueous solution has a concentration within a range from about 16 micrograms per milliliter (µg/ml) to about 40 µg/ml. The human serum includes, but is not limited to, a processed serum from Bioresource Technology, Inc., Weston, FL. For example, the human serum may be a mixture of human serum from a plurality of human individuals. In the method 100 of forming the nr-IGFBP-3 concentrate, contacting 120 the aqueous solution of either human serum or the IGF binding protein from the human serum with the porous matrix is configured to both buffer exchange and concentrate the nr-IGFBP-3 solution, as further described below. Contacting 120 the aqueous solution of either human serum or the IGF binding protein from the human serum with the porous matrix is further configured to facilitate one or more of desalting, enriching, and purifying the concentrated nr-IGFBP-3 aqueous solution. In some examples, the method 100 of forming a concentrate of nr-IGFBP-3 in aqueous solution is configured to facilitate large-scale batch processing of the nr-IGFBP-3 concentrate.

In some examples in accordance with the principles described herein, the porous matrix may be a solid or semi-solid material and may comprise an organic or inorganic, water insoluble material. The porous matrix may have any of a number of shapes such as, for example, tubular (e.g., column, hollow fiber, spiral wound, and hollow fine fiber), track-etched, or planar or flat surface (e.g., strip, disk, film, membrane, and plate). The porous matrix may be fabricated from a wide variety of materials, which may be naturally occurring or synthetic, polymeric or non-polymeric, fibrous or non-fibrous. The size of the pores of the porous matrix may be based on a nominal molecular weight limit (NMWL) or a nominal molecular weight cutoff (NMWC) of proteins in some examples.

For example, a NMWL or NMWC within a range of about 25 kDa to about 175 kDa may be used. In some examples, the NMWL or NMWC of the porous matrix may range from about 26 kDa to about 175 kDa, or about 27 kDa to about 175 kDa, or about 28 kDa to about 175 kDa, or about 29 kDa to about 175 kDa, or about 30 kDa to about 175 kDa, or about 40 kDa to about 175 kDa. In some examples, the NMWL or NMWC of the porous matrix may range from about 25 kDa to about 170 kDa, or about 25 kDa to about 165 kDa, or about 25 kDa to about 160 kDa, or about 25 kDa to about 155 kDa, or about 25 kDa to about 150 kDa. In an example, the NMWL or NMWC of the porous matrix may range from about 30 kDa to about 150 kDa.

In some examples, the porous matrix is part of a filtration device, wherein a sample is contacted with the porous matrix of the filtration device to separate targeted ingredients (e.g., proteins) of the sample from other ingredients based on the size or molecular weight of the ingredients in the sample, wherein the targeted ingredients are either preferentially retained on the porous matrix or pass through the porous matrix, and are then collected. Filtration techniques include, but are not limited to, microfiltration, ultrafiltration, or cross-flow or tangential flow filtration (TFF), for example. An example of ultrafiltration includes an AMICON® Stirred Cell equipped with a 30 kDa NMWL Ultrafiltration Disc (ULTRACEL® cellulose membrane) and a reservoir from EMD Millipore Corporation, Billerica, MA. An example of cross-flow or tangential flow filtration (TFF) includes a TFF System from Scilog, Inc., Middleton, WI, (e.g., PureTec TFF System), equipped with a TFF CENTRAMATE™ cassette having an OMEGA™ polyethersulfone (PES) membrane (30 kDa NMWC), from Pall Corporation, Port Washington, NY. In other examples, the porous matrix includes one or both of a sepharose-based resin in a chromatography column and one of the filtration devices described herein. The sepharose-based resin porous matrix facilitates one or more of hydrophobic interaction, ion exchange and affinity chromatography to separate ingredients in a sample, as is further described below.

Figure 2:
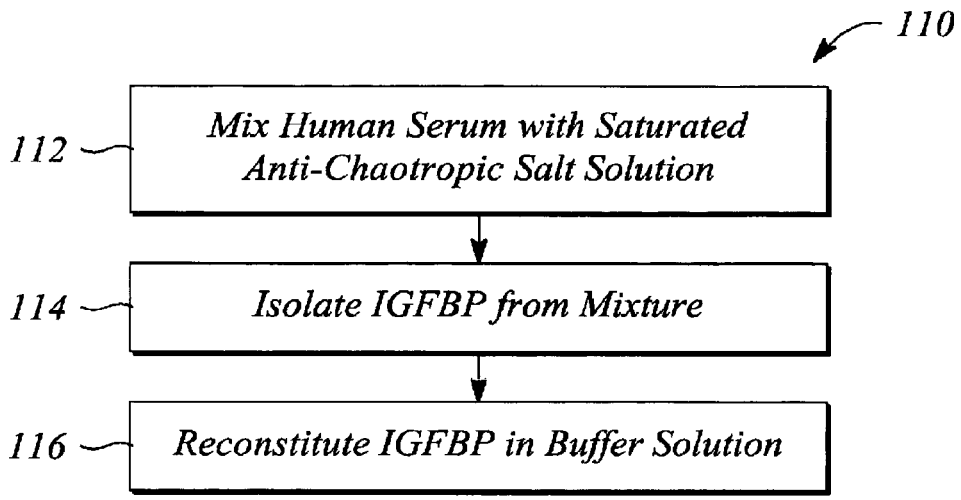
FIG. 2 illustrates a flow chart of providing a solution of IGF binding protein from human serum in an example, according to an embodiment consistent with the principles described herein.

Contacting an Aqueous Solution of IGF Binding Protein from Human Serum with Porous Matrix In some examples of the method 100 of forming a concentrate, the method 100 further comprises providing 110 an aqueous solution of IGF binding protein from the human serum, i.e., before contacting 120 the aqueous solution with the porous matrix. FIG. 2 illustrates a flow chart of providing 110 an aqueous solution of IGF binding protein from human serum in an example, in accordance with an embodiment of the principles described herein. As illustrated in FIG. 2, providing 110 an aqueous solution of IGF binding protein from human serum comprises mixing 112 the human serum with a saturated salt solution of an anti-chaotropic salt in an aqueous solvent, e.g., water, to form a mixture that includes precipitated IGF binding protein (IGFBP) from the human serum solution. The anti-chaotropic salt used in the method in accordance with the principles described herein is one that facilitates the function of precipitating proteins from solution based on the ionic strength of the anti-chaotropic salt.

For example, the Hofmeister series of ions provides a relative strength of ions in solution that facilitate precipitation by increasing the hydrophobic effects within the solution. In general, anti-chaotropic salts, such as ammonium sulfate, for example, expose hydrophobic areas of proteins by removing a highly structured water layer that, in solution, usually covers the hydrophobic areas. As a result, hydrophobic moieties on a protein molecule become available to more easily interact with hydrophobic moieties found on neighboring protein molecules. In some examples, the hydrophobic moieties may interact with hydrophobic ligands found in or on the porous matrix. In addition, anti-chaotropic salts may shield charged groups on the proteins, wherein the charged groups facilitate keeping proteins apart in solution, such that the solubility of proteins is reduced. Taken together, these effects lead to the formation of protein aggregates and the eventual precipitation (i.e., 'salting out') of proteins without causing irreparable denaturation of the proteins.

The solubility of different proteins is reduced to different extents depending on the anti-chaotropic strength of the salt and its concentration according to the Hofmeister series. The Hofmeister series in decreasing order of strength for an ability to salt out proteins, includes anions: $F^- \approx SO_4^{2-} > HPO_4^{2-} >$ acetate$> Cl^- > NO_3^- > Br^- > ClO_3^- > I^- > ClO_4^- > SCN^-$; and includes cations: $NH_4^+ > K^+ > Na^+ > Li^+ > Mg^{2+} > Ca^{2+} >$ guanidinium. As such, ammonium sulfate $((NH_4)_2SO_4)$ is considered a strong anti-chaotropic agent, while sodium chloride (NaCl) has less anti-chaotropic strength and effect than does ammonium sulfate, for example, for processing on a large-scale basis, to precipitate serum proteins, in particular IGFBP, out of solution. In some examples, the anti-chaotropic salt used in the saturated salt solution to precipitate out proteins during mixing 112 may be, but is not limited to, ammonium sulfate, potassium sulfate, sodium sulfate, magnesium sulfate, sodium phosphate, ammonium acetate, or a combination or mixture of two or more of these, for example.

In some examples, the amount of the human serum to the amount of the saturated salt solution in the mixture is about equal volumes, or a ratio of about 1 to about 1 (i.e., '1:1 ratio'). In other examples, the amounts in volume of human serum and saturated salt solution in the mixture may be different and may depend on one or more of the anti-chaotropic strength of the salt, the anti-chaotropic salt concentration, a size or scale of batch processing, and temperature of the sample or batch, by way of example and not limitation.

In some examples, the saturated salt solution of the anti-chaotropic salt may include, but is not limited to, sodium sulfate in water, or ammonium sulfate in water, or in some examples, sodium sulfate in an aqueous sodium phosphate solution, or ammonium sulfate in an aqueous sodium phosphate solution. A concentration of the saturated salt solution is that which is sufficient to precipitate out the IGF binding protein from the human serum solution. In some examples, the concentration of the saturated salt solution may range from about 0.25 grams/milliliter (g/ml) to about 1.0 g/ml, or about 0.25 g/ml to about 0.9 g/ml, or about 0.25 g/ml to about 0.8 g/ml. In some examples, the concentration of the saturated salt solution may range from about 0.3 g/ml to about 1.0 g/ml, or about 0.35 g/ml to about 1.0 g/ml, or about 0.4 g/ml to about 1.0 g/ml, or about 0.45 g/ml to about 1.0 g/ml, or about 0.5 g/ml to about 1.0 g/ml, or about 0.55 g/ml to about 1.0 g/ml, in some examples. In some examples, the concentration of the saturated salt solution may range from about 0.3 g/ml to about 0.8 g/ml.

In the examples of the saturated salt solution that comprises an anti-chaotropic salt in an aqueous sodium phosphate solution, a concentration of the sodium phosphate solution used in the saturated salt solution of the anti-chaotropic salt may be within a range of about 30 millimolar (mM) to about 60 mM, or about 35 mM to about 60 mM, or about 40 mM to about 60 mM, or about 45 mM to about 60 mM, or about 50 mM to about 60 mM. In some examples, the concentration of sodium phosphate solution used in the saturated salt solution may be within a range of about 30 mM to about 58 mM, or a range of about 30 mM to about 56 mM, or a range of about 30 mM to about 54 mM, or a range of about 30 mM to about 52 mM, or a range of about 30 mM to about 50 mM, or a range of about 30 mM to about 45 mM, or a range of about 40 mM to about 50 mM, or a range of about 45 mM to about 55 mM.

In some examples, the pH of the sodium phosphate solution may be within a range of about 7.0 and about 8.4, or a range of about 7.2 to about 8.4, or about 7.4 to about 8.4, or about 7.6 to about 8.4. In some examples, the pH of the sodium phosphate solution may be within a range of about 7.0 and about 8.2, or a range of about 7.0 to about 8.0, or about 7.0 to about 7.8, or about 7.0 to about 7.6. In an example, the concentration of the sodium phosphate solution is about 50 mM with a pH of about 7.4.

Moreover, the concentration of the anti-chaotropic salt in the sodium phosphate solution may range from about 25% to about 75% by weight of salt to volume of solution (i.e., 'by weight to volume'), or about 30% to about 75%, or about 35% to about 75%, or about 40% to about 75%, or about 45% to about 55% by weight to volume, for example. In some examples, the concentration of the anti-chaotropic salt in the sodium phosphate solution may range from about 25% to about 70%, or about 25% to about 65%, or about 25% to about 60%, or about 25% to about 55%, or about 25% to about 50% by weight to volume. In an example, the saturated salt solution comprises ammonium sulfate as the anti-chaotropic salt in about a 50 mM sodium phosphate solution with a concentration of about 50% by weight to volume of ammonium sulfate.

As further illustrated in FIG. 2, providing 110 an aqueous solution of IGF binding protein further comprises isolating 114 the precipitated IGF binding protein from the mixture. The precipitated IGF binding protein may be isolated 114 comprising centrifuging the mixture of human serum in the saturated salt solution; and removing a supernatant comprising the saturated anti-chaotropic salt solution from the precipitated IGF binding protein, which may be in a form of a pellet, that separated from the solution, for example. Various centrifuge equipment may be used for isolating 114 the precipitated IGF binding protein from the mixture including, but not limited to, SORVALL™ centrifuges from Thermo Fisher Scientific, Inc., Waltham, MA, or ADVANTI™ centrifuges from Beckman Coulter, Inc., Indianapolis, IN.

Moreover, as illustrated in FIG. 2, providing 110 an aqueous solution of IGF binding protein further comprises reconstituting 116 the isolated IGF binding protein pellet by dissolving the pellet in an aqueous buffer solution. The reconstituted 116 IGF binding protein (IGFBP) precipitate or pellet is the provided 110 IGFBP solution that is contacted 120 with the porous matrix in the method 100 of forming a concentrate of FIG. 1A. Various buffer solutions may be used for reconstituting 116 the isolated IGF binding protein pellet or precipitate including, but not limited to, a phosphate buffered saline solution (PBS) or PBS solution that includes sodium azide. In some examples, the aqueous buffer solution comprises PBS with a range of about 0.05% to about 15% by weight sodium azide to volume of solution ('weight to volume'), or PBS with a weight to volume range of about 0.06% to about 15% sodium azide, or about 0.08% to about 15% sodium azide, or about 0.10% to about 15% sodium azide, or about 0.05% to about 13% sodium azide, or about 0.05% to about 12% sodium azide, or about 0.05% to about 10% sodium azide. In an example, the aqueous buffer solution comprises PBS with about 0.09% sodium azide by weight to volume used to dissolve the pellet to provide 110 the aqueous solution of IGF binding protein.

In the embodiments that include the provided 110 solution of IGF binding protein (IGFBP) from human serum, as described above with respect to FIG. 2, the porous matrix used in contacting 120 is a filtration membrane including, but not limited to, an ultrafiltration disc, a tangential flow filtration (TFF) membrane, or a combination thereof, for example. The ultrafiltration disc may be in a filtration device, such as the AMICON® Stirred Cell from EMD Millipore Corp., described herein, for example. The TFF membrane may be a membrane of a single pass filtration system or a crossflow filtration system, for example, and may be a TFF system from Scilog, Inc., as described herein, or from Membrane Specialists, Hamilton, OH, or EMD Millipore Corp., for example. In some examples, the reconstituted 116 IGFBP precipitate in the provided 110 solution may further comprise other serum proteins that also precipitated during mixing 112. During contacting 120, the porous matrix will filter out serum proteins in the provided 110 IGFBP solution having a molecular weight that is one or both of greater than or less than the NMWC or NMWL of the porous matrix for nr-IGFBP. Moreover, the concentrated nr-IGFBP-3 in aqueous solution that is collected 140 from the porous matrix also may include some serum proteins (e.g., proteins having a substantially similar molecular weight to nr-IGFBP-3, including other IGF binding proteins) that were not filtered by the porous matrix during contacting 120. Since nr-IGFBP-3 is the most abundant IGF binding protein found in human serum, for simplicity of discussion only herein, the protein concentrate that is collected 140 in these embodiments will be referred to as 'nr-IGFBP-3' with the understanding that the concentrated nr-IGFBP-3 solution may also comprise other proteins. Moreover, the collected 140 nr-IGFBP-3 concentrate has the native heterogeneous form, as described above.

Moreover, in these embodiments, contacting 120 the provided 110 IGFBP solution with the porous matrix comprises applying the IGFBP solution to the porous matrix and flushing the porous matrix with an aqueous buffer solution to filter and to both buffer exchange the IGFBP solution and concentrate the IGFBP solution into the nr-IGFBP-3 concentrate. In some examples, the aqueous buffer solution used to flush the porous matrix and provide a buffer exchange includes, but is not limited to, PBS or PBS that includes sodium azide. For example, the collected 130 nr-IGFBP-3 is buffer exchanged using PBS with sodium azide (e.g., PBS with about 0.09% sodium azide by weight to volume). In some examples, the aqueous buffer solution used to flush the porous matrix and provide the buffer exchange is substantially similar to the aqueous buffer solution and concentration ranges, as described above, used to reconstitute 116 the IGF binding protein pellet.

Contacting an Aqueous Solution of Human Serum with Porous Matrix

Figure 1B:
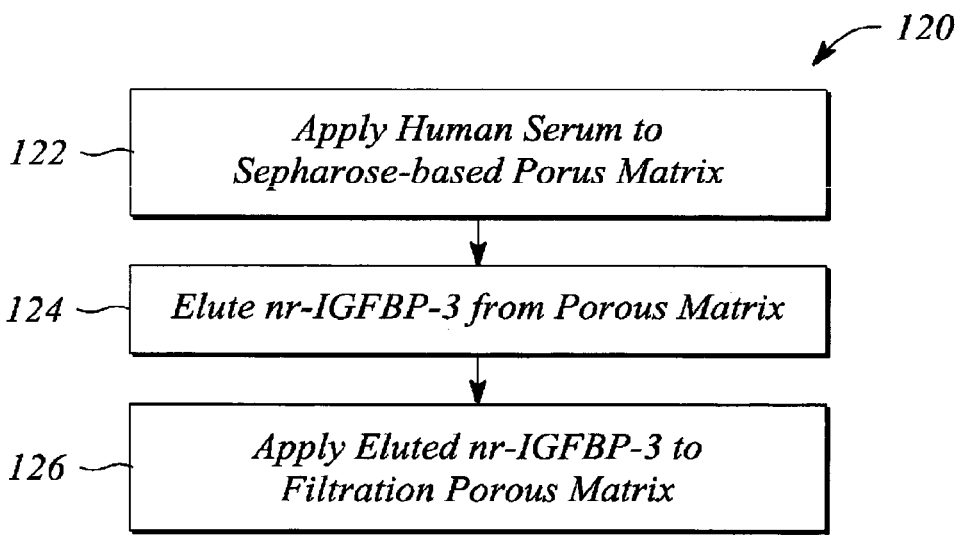
FIG. 1B illustrates a flow chart of a process of contacting an aqueous solution of human serum with a porous matrix in the method of FIG. 1A in an example, according to an embodiment consistent with the principles described herein.

Referring again to FIG. 1A, in other embodiments according to the principles herein, the method 100 of forming a concentrate of nr-IGFBP-3 in aqueous solution comprises contacting 120 an aqueous solution of human serum with a porous matrix that comprises a sepharose-based resin. FIG. 1B illustrates a flow chart of a process of contacting 120 the aqueous solution of human serum with the porous matrix in the method of FIG. 1A in an example, in accordance with the principles described herein. In these embodiments, human serum is mixed with a first buffer solution. The first buffer solution may contain a buffer including, but not limited to, any of the buffers mentioned above having a substantially neutral pH buffering capacity, in particular, in a pH range of 7 to 9. Contacting 120 the human serum in the first buffer solution comprises applying 122 the human serum in the first buffer solution to the sepharose-based porous matrix in a chromatography column that has been equilibrated with a second buffer solution that also has a neutral buffering capacity, in particular, in a pH range of 7 to 9.

The sepharose-based resin may include, but is not limited to, Hydrophobic Interaction Chromatography (HIC) resins such as butyl sepharose, phenyl sepharose, or octyl sepharose, Ion-Exchange resins such as SP-sepharose or Q-sepharose, or Affinity chromatography resin such as Heparin sepharose. Any one or a combination or mixture of two or more of these, for example, may be used according to the principles described herein. In some examples, the sepharose-based resin is selected from a group consisting of butyl sepharose and phenyl sepharose in an HIC column. The sepharose-based resin is packed and equilibrated in a chromatography column using the above-mentioned second buffer solution.

The first buffer solution and the second buffer solution may have the same ingredients, albeit in different concentrations, or may be different buffer solutions. In some examples, the first buffer solution and the second buffer individually includes, but is not limited to, a phosphate-containing buffer, an ammonium sulfate-containing buffer, Tris, or a mixture of Tris and either ammonium sulfate or ammonium phosphate, for example. In some examples, the first buffer solution and the second buffer solution are aqueous solutions of Tris and an anti-chaotropic salt, such as ammonium sulfate, for example. The first buffer solution and the second buffer solutions each have a concentration configured to keep the serum proteins in solution, in particular the IGF binding protein in the human serum (i.e., does not salt out the proteins). Moreover, the concentration of the first buffer solution and the second buffer solution are each configured to increase the solubility of the various serum proteins (e.g., rendering them more ionic) more so than that of the IGF binding proteins, and in particular, the nr-IGFBP-3. This is so because a major impurity that this embodiment targets to remove is human serum albumin and many other serum proteins from the nr-IGFBP-3. As such, a majority of human serum albumin and many other serum proteins, which are targeted for separation and removal, will flow through the sepharose-based column and allow for substantial sepharose resin capacity to bind to the serum protein of interest, i.e., the nr-IGFBP-3.

The choice of buffer solutions and the concentration thereof may be dependent on factors including, but not limited to, one or more of the choice of sepharose-based resin used, the type of chromatography used, the proteins to be separated out of the human serum, the batch size being eluted in the chromatography column, and the anti-chaotropic salt strength, for example. In some examples, the human serum solution is a mixture of about a 1:1 volume ratio of the human serum and the first buffer solution. In these examples, the concentration of the first buffer solution is about twice the concentration of the second buffer solution used to equilibrate the sepharose-based column. The second buffer solution has less anti-chaotropic strength so that a fraction of the human serum that is targeted for removal from the contacted 120 solution will remain unbound ('the unbound fraction') and wash through the chromatography column, while a remaining fraction of the contacted 120 solution will be bound ('the bound fraction') to the sepharose-based resin until subsequent removal. As such, the bound fraction will substantially only include the IGF binding protein, and in particular, the nr-IGFBP-3 separated from the other serum proteins.

In some examples, the first buffer solution that is mixed with the human serum solution comprises an aqueous solution of Tris and ammonium sulfate $((NH_4)_2SO_4)$ salt. The Tris and ammonium sulfate concentrations in the first buffer solution at room temperature may be within a range of about 30 mM to about 70 mM Tris and about 0.5 M to about 2.0 M ammonium sulfate. In some examples, the Tris and ammonium sulfate concentrations in the first buffer solution at room temperature may be within a range of about 35 mM to about 70 mM Tris and about 0.6 M to about 2.0 M ammonium sulfate, or about 40 mM to about 70 mM Tris and about 0.7 M to about 2.0 M ammonium sulfate, or about 45 mM to about 70 mM Tris and about 0.8 M to about 2.0 M ammonium sulfate, or about 50 mM to about 70 mM Tris and about 1.0 M to about 2.0 M ammonium sulfate. In some examples, the Tris and ammonium sulfate concentrations in the first buffer solution at room temperature may be within a range of about 30 mM to about 65 mM Tris and about 0.5 M to about 1.8 M ammonium sulfate, or about 30 mM to about 60 mM Tris and about 0.5 M to about 1.5 M ammonium sulfate, or about 30 mM to about 55 mM Tris and about 0.5 M to about 1.0 M ammonium sulfate, or about 30 mM to about 50 mM Tris and about 0.5 M to about 0.75 M ammonium sulfate.

The second buffer solution that also comprises an aqueous solution of Tris and ammonium sulfate salt will have respective concentrations in the second buffer solution at room temperature that may be within a range of about 18 mM to about 35 mM Tris and about 0.3 M to about 1.0 M ammonium sulfate, or about 20 mM to about 35 mM Tris and about 0.35 M to about 1.0 M ammonium sulfate, or about 22 mM to about 35 mM Tris and about 0.4 M to about 1.0 M ammonium sulfate, or about 25 mM to about 35 mM Tris and about 0.5 M to about 1.0 M ammonium sulfate. In some examples, the Tris and ammonium sulfate concentrations in the second buffer solution at room temperature may be within a range of about 15 mM to about 32 mM Tris and about 0.25 M to about 0.9 M ammonium sulfate, or about 15 mM to about 30 mM Tris and about 0.25 M to about 0.75 M ammonium sulfate, or about 15 mM to about 27 mM Tris and about 0.25 M to about 0.5 M ammonium sulfate, or about 15 mM to about 25 mM Tris and about 0.25 M to about 0.37 M ammonium sulfate.

In some examples, the pH of the first buffer solution and the second buffer solution is within a range of about pH 7.0 to about 9.0, or about pH 7.5 to about 9.0, or about 7.8 to about 9.0, or about pH 8.0 to about 9.0, or about pH 7.5 to about 8.7, or about pH 7.5 to about 8.5, or about pH 7.5 to about pH 8.3. In an example, the sepharose-based resin used is phenyl sepharose in an HIC column for protein separation, and the first buffer and the second buffer each comprises a mixture of Tris and ammonium sulfate. The first buffer solution has a concentration of about 50 mM Tris and about 0.7 M ammonium sulfate with a pH of about 8.1 and the second buffer solution has a concentration of about 25 mM Tris and about 0.35 M ammonium sulfate with a pH of about 8.1. In some examples, the concentration of the first buffer solution is twice the concentration of the second buffer solution.

The chromatography column is configured to separate the nr-IGFBP-3 from the human serum (including from other proteins in the human serum, such as serum albumin, for example) using hydrophobic interaction chromatography (HIC) in some examples. As such, the chromatography column may also be configured to one or both purify the nr-IGFBP-3 and enrich the nr-IGFBP-3. Further information regarding the use of HIC and a sepharose-based resin porous matrix is found in U.S. Pat. No. 7,307,148, which is incorporated by reference in its entirety herein.

In some examples, applying 122 the human serum in first buffer solution to the chromatography column comprises application of the solution at a rate within a range of about 1.0 milliliter per minute (ml/min) to about 5.0 ml/min to the second buffer-equilibrated sepharose-based resin porous matrix. In some examples, the solution of human serum in first buffer may be applied 122 at a rate within a range of about 1.4 ml/min to about 5.0 ml/min, or about 1.8 ml/min to about 5.0 ml/min, or about 2.0 ml/min to about 5.0 ml/min. In some examples, the rate of application 122 of the human serum in the first buffer solution is within a range of or about 1.0 ml/min to about 4.6 ml/min, or about 1.0 ml/min to about 4.2 ml/min, or about 1.0 ml/min to about 3.8 ml/min, or about 1.0 ml/min to about 3.6 ml/min. In an example, the solution of human serum in the first buffer is applied 122 to the porous matrix of the chromatography column at a rate of about 3.0 ml/min. Contacting 120 the human serum solution further comprises washing the unbound fraction of the applied 122 human serum solution through the chromatography column with the second buffer solution to remove the unbound fraction from the column.

Moreover, as illustrated in FIG. 1B, in these embodiments, contacting 120 the solution of human serum in first buffer with the porous matrix further comprises eluting 124 the bound fraction of the applied 122 human serum in first buffer solution with a third buffer solution. As mentioned above, in these embodiments, the bound fraction includes substantially only IGF binding protein, in particular, the nr-IGFBP-3 that is separated from a remainder of the human serum that includes the other serum proteins in the unbound fraction of the applied 122 human serum in first buffer solution. Moreover, the nr-IGFBP-3 in the bound fraction has the native heterogeneous form, as described above.

The third buffer solution is different from one or both of the first buffer solution and the second buffer solution in that it contains little to no anti-chaotropic salt (e.g., substantially 0% anti-chaotropic salt). For example, the third buffer solution may contain a buffer including, but not limited to, any of the buffers mentioned above, or another buffer that has a buffering capacity between about pH 7 to about pH 9. In some examples, the third buffer comprises Tris without ammonium sulfate salt in order to elute 124 the bound fraction of nr-IGFBP-3 from the sepharose-based column.

In some examples, the third buffer solution comprises Tris (and no anti-chaotropic salt) in a concentration within a range of about 15 mM to about 35 mM, or about 15 mM to about 30 mM, or about 15 mM to about 27 mM, or about 15 mM to about 25 mM, or about 20 mM to about 30 mM. The pH of the third buffer solution is within a range of about pH 7.5 to about 8.6, for example. In some examples, the pH of the third buffer solution is within a range of about pH 7.6 to about 8.6, or about pH 7.7 to about 8.6, or about pH 7.5 to about 8.4, or about pH 7.5 to about 8.3, or about pH 7.5 to about 8.2. In an example, the third buffer solution has a concentration of about 25 mM Tris and a pH of about 8.1. In some examples, the pH of each of the first buffer solution, the second buffer solution and the third buffer solution is not less than pH 7.0, or is not less than pH 7.4, or is not less than pH 7.6, or is not less than pH 7.8, or is not less than pH 8.0.

Referring again to FIG. 1B, in some examples, contacting 120 an aqueous solution of human serum with a porous matrix may further comprise applying 126 the eluted nr-IGFBP-3 in third buffer solution to a porous matrix of a filtration system or device with a buffer exchange solution to filter, buffer exchange and concentrate the applied 126 nr-IGFBP-3 solution. The buffer exchange solution includes, but is not limited to, PBS or PBS mixed with sodium azide, for example. The buffer exchange solution may be substantially similar to the buffer exchange solutions and concentration ranges described above.

The filtration system used in applying 126 the eluted 124 nr-IGFBP-3 in the third buffer solution includes, but is not limited to, any of the filtration systems described above. In some examples, one or more of the AMICON® Stirred Cell ultrafiltration system, the TFF System, and another microfiltration, ultrafiltration or cross-flow filtration system may be used. Moreover, the filtration membrane may include using a NMWL or NMWC membrane of about 10 kDa to about 20 kDa to filter, buffer exchange and concentrate the nr-IGFBP-3 in solution. In some examples, the nr-IGFBP-3 solution may be passed over the filtration membrane with the buffer exchange solution in sequential steps or in a continuous manner to facilitate concentrating the nr-IGFBP-3 in aqueous solution, depending on the filtration system used. For example, a TFF system applies 126 the eluted nr-IGFBP-3 solution in a continuous manner to buffer exchange and concentrate the nr-IGFBP-3 solution.

Referring again to FIG. 1A, as mentioned above, the method 100 of forming a concentrate of nr-IGFBP-3 further comprises collecting 140 concentrated nr-IGFBP-3 in aqueous solution from the porous matrix of the filtration system used. The concentrated nr-IGFBP-3 aqueous solution made by the method 100 of forming a concentrate according to the embodiments described herein has a concentration range of from about 16 micrograms per milliliter (µg/ml) to about 40 µg/ml. The method 100 of forming a concentrate of nr-IGFBP-3 described herein is configured to facilitate making large-scale batches of the nr-IGFBP-3 concentrate. In some examples, the concentrated nr-IGFBP-3 solution may be substantially similar to the human IGF binding protein stock solution described above. As such, the concentrated nr-IGFBP-3 solution made by the method 100 of forming a concentrate herein may be within any of the concentration ranges described above for the human IGF binding protein stock solution. In particular, the concentrated nr-IGFBP-3 aqueous solution is significantly more concentrated than an amount of nr-IGFBP-3 found in or isolated from human serum, which typical ranges from about 3.5 µg/ml to 5.5 µg/ml.

The concentration range of the concentrated nr-IGFBP-3 solution made by the method 100 herein is sufficient to make a set of nr-IGFBP-3 calibrators having different concentrations configured to span a suspected range of concentrations of IGFBP-3 analyte in an IGFBP-3 analyte immunoassay of human patient samples. In some examples, the concentration of nr-IGFBP-3 in each calibrator of the set is different, and the different concentrations of the nr-IGFBP-3 in the calibrator set are within a range of from about 0.5 µg/ml to about 16 µg/ml. In some examples, the set of nr-IGFBP-3 calibrators is substantially similar to the set of calibration standards described above. As such, the concentration range of nr-IGFBP-3 in the different calibrators may be within any of the concentration ranges described above for the set of calibration standards.

In some examples, the different nr-IGFBP-3 calibrators in the set may comprise one or more of a 0.50 µg/ml nr-IGFBP-3 calibrator, a 1.0 µg/ml nr-IGFBP-3 calibrator, a 1.5 µg/ml nr-IGFBP-3 calibrator, a 2.0 µg/ml nr-IGFBP-3 calibrator, a 2.5 µg/ml nr-IGFBP-3 calibrator, a 3.0 µg/ml nr-IGFBP-3 calibrator, a 3.5 µg/ml nr-IGFBP-3 calibrator, a 4.0 µg/ml nr-IGFBP-3 calibrator, a 4.5 µg/ml nr-IGFBP-3 calibrator, a 5.0 µg/ml nr-IGFBP-3 calibrator, a 5.5 µg/ml nr-IGFBP-3 calibrator, a 6.0 µg/ml nr-IGFBP-3 calibrator, a 7.0 µg/ml nr-IGFBP-3 calibrator, an 8.0 µg/ml nr-IGFBP-3 calibrator, a 9.0 µg/ml nr-IGFBP-3 calibrator, a 10.0 µg/ml nr-IGFBP-3 calibrator, a 12.0 µg/ml nr-IGFBP-3 calibrator, a 14.5 µg/ml nr-IGFBP-3 calibrator, and a 16.0 µg/ml nr-IGFBP-3 calibrator. The nr-IGFBP-3 concentrations in the set of calibrators are configured to span a suspected concentration range of the IGFBP-3 analyte levels in human patient samples. In some examples, the different nr-IGFBP-3 calibrators in the set may include or further include calibrators having concentrations of nr-IGFBP-3 that fall between any of the concentration values listed above. Moreover, in some examples, various lower concentration nr-IGFBP-3 calibrators may provide MDP standards for the set of calibrators.

Since the nr-IGFBP-3 ternary complex comprises bound IGF-1 or IGF-2 and ALS and glycosylated units, it is further within the scope of some embodiments of the principles described herein for different nr-IGFBP-3 calibration standards to be prepared to facilitate measurement of IGF-1 or IGF-2 analyte levels in immunoassays of human patient samples. In some examples, the set of nr-IGFBP-3 calibrators prepared from the IGF binding protein stock solution, as described above, further facilitates measurement of IGF-1 or IGF-2 analyte levels that may range from about 20 nanograms per milliliter (ng/ml) to about 375 ng/ml of IGF-1 of IGF-2. The amount of IGF-1 or IGF-2 complexed with the nr-IGFBP-3 is substantially directly proportional, for example. As such, a set of IGF-1 or IGF-2 calibration standards can be prepared using the nr-IGF binding protein stock solution described herein. For example, a set of IGF-1 or IGF-2 calibration standards having different concentrations of IGF-1 or IGF-2 that span a suspected range of IGF-1 or IGF-2 levels in patient samples of about 100 ng/ml to about 750 ng/ml may be prepared with a corresponding set of nr-IGFBP-3 calibrators that have different concentrations of nr-IGFBP-3 that range from about 5 µg/ml to 40 µg/ml from the IGF binding protein stock solution having the concentration range of about 16 µg/ml to about 40 µg/ml.

Further, as mentioned above, the nr-IGFBP-3 calibrators are diluted with a human serum. In some examples, it may be desirable to have substantially IGF binding protein-free human serum as the diluent to facilitate achieving targeted levels of nr-IGFBP-3 in calibration standards and controls. In some embodiments, the phrase 'substantially IGF binding protein-free' means that an amount of IGF binding proteins in the human serum is substantially below LOQ, which may be set at about 100 ng/ml or at about 200 ng/ml. In some embodiments, the substantially IGF binding protein-free human serum contains no more than about 5% (by volume), or no more than about 2%, or no more than about 0.20 µg/mL, or about 0% of IGF binding protein, as defined herein.

A Method of Making Substantially IGF Binding Protein-Free Human Serum

Figure 3:
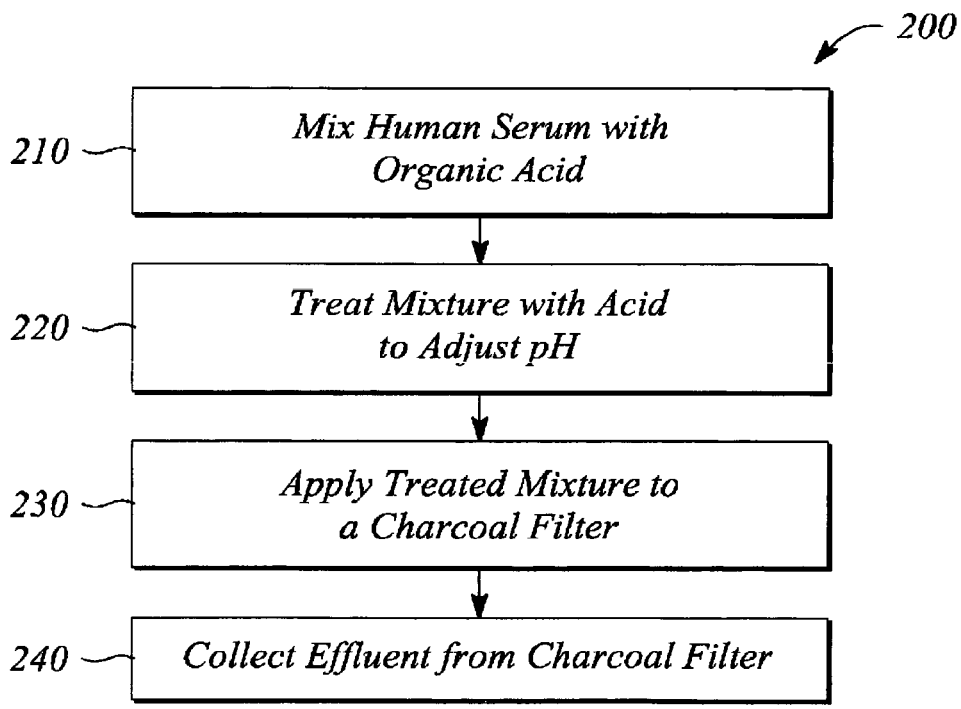
FIG. 3 illustrates a flow chart of a method of making a human serum diluent that is substantially free of insulin-like growth factor (IGF) binding protein in an example, according to an embodiment consistent with the principles described herein.

A method 200 of making a human serum diluent that is substantially free from IGF binding protein is illustrated in FIG. 3 in an example, in accordance with the principles described herein. The method 200 of making a substantially IGF binding protein-free human serum diluent comprises mixing 210 human serum with an organic acid, such as acetic or citric acid, or an amino acid (e.g., glycine), or an inorganic acid, such as hydrochloric acid; and treating 220 the mixture with the acid to adjust a pH to be, for example, less than about pH 3.5, but not less than pH 2.0. For example, the mixture may be adjusted to a pH of about pH 3.0 during treating 220. Excess acid treatment to lower the pH to less than pH 2.0 may result in severe protein aggregation, for example.

The method 200 of making a substantially IGF binding protein-free human serum diluent further comprises applying 230 the acid-treated mixture of human serum onto a charcoal filter. The charcoal filter may be a MILLISTAK+® charcoal cartridge filter from EMD Millipore, for example. In some examples, the acid-treated mixture may be loaded on the charcoal filter at a rate of about 1.5 ml/min, or about 2.0 ml/min, or about 2.5 ml/min, or about 3.0 ml/min. The method 200 of making a substantially IGF binding protein-free human serum diluent further comprises collecting 240 effluent from the charcoal filter. The collected 240 effluent is an unbound fraction of acid-treated mixture that is the substantially IGF binding protein-free human serum.

In some examples, the method 200 further comprises adjusting the pH of the collected 240 effluent to be within a range of about pH 7.25 to about pH 7.50, for example, and performing a buffer exchange to the pH-adjusted collected 240 effluent. In some examples, the buffer exchange is performed using a porous matrix such as an AMICON® Stirred Cell or a TFF system in a PBS buffer solution, for example, a solution of PBS and sodium azide, as described above. The buffer exchanged effluent provides a human serum diluent that is substantially free from IGF binding protein, for example, for use in preparing the nr-IGFBP-3 calibration standards, as described herein.

General Description of Assays in which the Calibrators May be Utilized

The following discussion is by way of illustration and not limitation. The present compositions may be employed in any assay for the determination of IGF and IGFBP-3 where calibrators are employed. An assay can be performed either without separation (homogeneous) or with separation (heterogeneous) of any of the assay components or products. Heterogeneous assays usually involve one or more separation steps and can be competitive or non-competitive. Immunoassays may involve labeled or non-labeled reagents. Immunoassays involving non-labeled reagents usually comprise the formation of relatively large complexes involving one or more antibodies prepared from immunogenic conjugates in accordance with the principles described herein. Such assays include, for example, immunoprecipitin and agglutination methods and corresponding light scattering techniques such as, e.g., nephelometry and turbidimetry, for the detection of antibody complexes. Labeled immunoassays include, but are not limited to, chemiluminescence immunoassays, enzyme immunoassays, fluorescence polarization immunoassays, radioimmunoassays, inhibition assays, induced luminescence assays, and fluorescent oxygen channeling assays, for example. In the assay, the results are compared to a set of calibrators and a determination of the concentration of analyte in a sample is made.

The sample to be tested is any sample that may contain one or both of IGF and IGFBP-3 including, but not limited to, biological material, such as, for example, body fluid and body tissue, which is obtained from the body of a mammal including humans, birds, reptiles, and other vertebrates. Body fluids include, for example, whole-blood, plasma, serum, lymphatic fluid, or umbilical cord blood, for example.

The assay is conducted by combining a sample and reagents for conducting the assay in an assay medium. The nature and amounts of these assay reagents depend on the nature of the assay being performed. For example, assay reagents for sandwich immunoassays include at least two antibodies, at least one of which is labeled. For competitive immunoassays, the assay reagents include at least one antibody and an analyte analog, which usually differs from the analyte by comprising a label. The assay medium is an aqueous buffered medium at a moderate pH, and is generally one that provides optimum assay sensitivity. The aqueous medium may be solely water or may include from 0.1 to about 40 volume percent of a cosolvent such as, for example, a water miscible organic solvent, e.g., an alcohol, an ether or an amide. The pH for the medium will usually be in the range of about 4 to about 11, or in the range of about 5 to about 10, or in the range of about 6.5 to about 9.5, for example.

EXAMPLES

Unless otherwise indicated, materials in the experiments below may be purchased from the Sigma-Aldrich Chemical Corporation (St. Louis MO). Parts and percentages disclosed herein are by weight to volume unless otherwise indicated.

Example 1: Nr-IGFBP-3 Enrichment by Sodium Sulfate Precipitation

Saturated sodium sulfate solution was prepared by mixing 60 grams (g) of sodium sulfate (Sigma-Aldrich, catalog number (cat no.) 238597, molecular weight (mw) equal to 142.04, solubility in water at 20° C. equal to 19.5 g/100 ml water) with 200 ml water at room temperature for 2 hours. Undissolved sodium sulfate salt was removed by filtration with a 0.2 micron or micrometer (µm) filter. Highly Normalized Human Serum ('BRT' or 'BRT1') (200 ml) from Bioresource Technology, cat no. H1090, lot number 1407033, was filtered to a 0.2 µm filter and allowed to warm to room temperature.

The saturated sodium sulfate solution (200 ml) was mixed with an equal volume of the BRT1 for 1 hour at room temperature on a low speed mixer to avoid foaming. An aliquot of 25 ml was poured to a Falcone tube and centrifuged at 3,000 times g (i.e., where g=9.8 meters per second squared (m/s$^2$) is the acceleration due to the earth's gravity) at 4° C. for one hour using a Thermo Fisher SORVALL™ Centrifuge, model ST40R. The supernatant from each tube was then carefully removed by a vacuum aspirator, and the remaining pellet was dissolved in PBS/0.09% Sodium Azide. The re-dissolved or reconstituted pellet (approximately 200 ml) was put to a 200 ml AMICON® Stirred Cell (model 8200, Millipore, cat no. 6028) which was equipped with a 30 kilo Dalton (KDa) NMWL Ultrafiltration Disc (Millipore cat no. PLTK06210) and an RC800 Mini-Reservoir (Millipore cat no. 5123), and buffer-exchanged into PBS/0.09% sodium azide. The buffer exchange was completed after greater than or equal to 1000 ml, 5 times the pellet-dissolved solution, of PBS/0.09% sodium azide effluent waste was collected.

The solution in the AMICON® Stirred Cell was further concentrated down 10-15 ml using the AMICON® Stirred Cell and the nr-IGFBP-3 concentration was measured by a CENTAUR® XP prototype IGFBP-3 assay system (Siemens Healthcare GmbH) with standards value-assigned by an IMMULITE® 2000 Immunoassay System (Siemens Healthcare GmbH). The nr-IGFBP-3 concentrate was mixed with BRT1, 1:1 or different proportions, to build a first set of seven standards (hereinafter referred to as 'BL5U' standards) in 2.5% bovine serum albumin (BSA) based Base Pool.

Table 1 lists the sodium sulfate-precipitated BL5U standards 'S01-S07' with the value-assigned dose values of each BL5U standard in serum, wherein S01 is a 'blank standard' with no added nr-IGFBP-3, and further lists relative light units (RLUs) measured for each BL5U standard, and a signal to noise ratio (S/N) for each BL5U standard. The RLU refers to specific chemiluminescence from the nr-IGFBP-3 measured by the prototype CENTAUR® system for the seven BL5U standards. The S/N for the blank standard S01 was designated as equal to 1.0, and the S/N of each of BL5U standards S02-S07 is equal to their measured RLU divided by the blank standard RLU. A BL5U low dose calibrator 'BL5U Low Cal' and BL5U high dose calibrator 'BL5U High Cal' were used to calculate dose values of nr-IGFBP-3 in 'unknown' patient samples using a 2-point data fitting calibration program.

Table 1 shows that sodium sulfate salt as the anti-chaotropic agent was capable of precipitating nr-IGFBP-3 out of solution from human serum (along with other serum proteins), albeit with a lower precipitation yield than when ammonium sulfate salt was used as the anti-chaotropic agent, as shown in Table 3 below with respect to Example 2. Table 1 also shows that the prototype CENTAUR® IGFBP-3 assay (ADVIA) was capable of detecting nr-IGFBP-3 in a dose-dependent manner with BL5US06 (at 8.6 µg/ml) and BL5US07 (15.3 µg/ml) having nr-IGFBP-3 doses far greater than that in the starting BRT human serum (i.e. about. 4.0-4.5 µg/ml). Therefore, the use of an anti-chaotropic salt such as sodium sulfate is capable of concentrating nr-IGFBP-3 from human serum by precipitation of the analyte out of solution (along with other serum proteins), followed by resolublization of the precipitated analyte, then concentration and buffer exchange using either ultrafiltration, or even TFF. However, the final yield of precipitated/re-solubilized nr-IGFBP-3 using sodium sulfate salt as the anti-chaotropic agent decreased with increasing scale (batch size) of the precipitation reaction (i.e., starting volume of BRT human serum plus the concentrated anti-chaotropic salt solution).

TABLE 1

BL5U RLU Signal to Noise (S/N) Ratios Using IMMULITE®-Value Assigned Standards

| Standards Sample | Dose/Value (µg/ml) | RLU | S/N |
|---|---|---|---|
| BL5US01 | 0.0 | 8901 | 1.0 |
| BL5US02 | 0.4 | 162535 | 18.3 |
| BL5US03 | 0.7 | 286781 | 32.2 |
| BL5US04 | 2.1 | 664339 | 74.6 |
| BL5US05 | 4.9 | 1195997 | 134.4 |

TABLE 1-continued

BL5U RLU Signal to Noise (S/N) Ratios Using IMMULITE ®-Value Assigned Standards

| Standards Sample | Dose/Value (µg/ml) | RLU | S/N |
|---|---|---|---|
| BL5US06 | 8.6 | 1691969 | 190.1 |
| BL5US07 | 15.3 | 2273676 | 255.4 |

BL5U Low Cal = 0.38 µg/ml,
BL5U High Cal = 9.00 µg/ml
RLU = relative light units

Example 2: Nr-IGFBP-3 Enrichment by Ammonium Sulfate Precipitation

Example 2A

A saturated ammonium sulfate solution was prepared by mixing 160 g of ammonium sulfate (Sigma-Aldrich, cat no. 2939, mw equal to 132.14, solubility in water at 20° C. equal to 75.4 g/100 ml water) with 200 ml water and allowed to mix at room temperature for 2 hours. After the ammonium sulfate solution was filtered to a 0.2 µm filter, 200 ml of the solution was mixed with equal volume of BRT which was also pre-warmed to room temperature. The rest of procedure was the same as what was described in the Example 1.

Example 2B 400 ml BRT was used with an equal volume of the Example 2A saturated ammonium sulfate solution and the same procedure described in Example 1 was followed. The enriched nr-IGFBP-3 concentrates were combined and made into a second set of seven standards (hereinafter referred to as 'BL7'), numbered S01-S07 and low value and high value calibrators, which were also value assigned by the IMMU-LITE® 2000 IGFBP-3 assay system. BL7S07 was value assigned first using the IMMULITE® IGFBP-3 assay (i.e., a suitable predicate device). BL7S07 was then diluted serially using nr-IGFBP-3-free buffer. The 'BL7 Low Cal' and 'BL7 High Cal' values were used for calculating dose values of nr-IGFBP-3 concentration found in 'unknown' patient samples using a Low Cal and High Cal 2-point data fitting calibration program.

Figure 4:
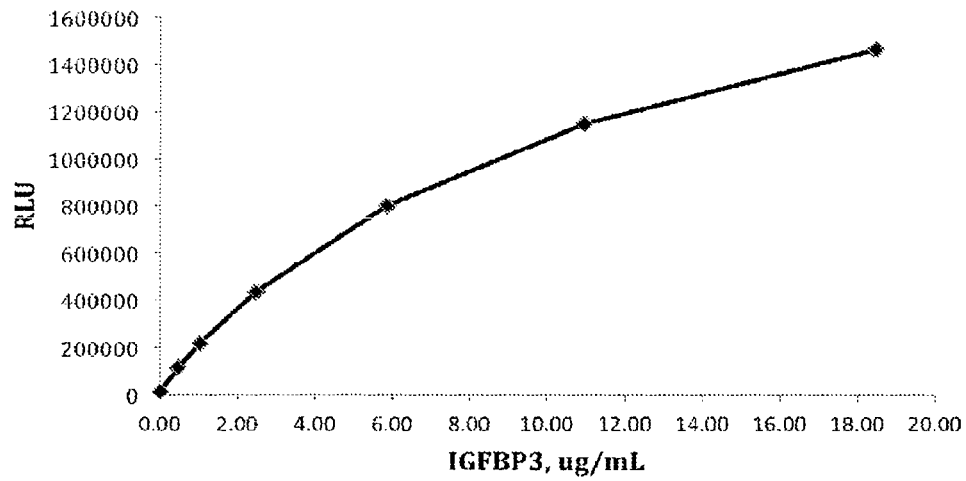
FIG. 4 illustrates a graph of ammonium sulfate-precipitated nr-IGFBP-3 dose response in relative light units (RLU) from prototype CENTAUR® XP assay versus IMMU-LITE® value-assigned standards in an example, according to an embodiment consistent with the principles described herein.

Table 2 lists the BL7 standards 'S01-S07' with the value-assigned dose values of each BL7 standard in serum, wherein S01 is a 'blank standard' with no added nr-IGFBP-3, and further lists RLUs measured for each BL7 standard, and a S/N for each BL7 standard. The low dose value and high dose value are also listed for the BL7 Low Cal and the BL7 High Cal. FIG. 4 illustrates a graph of ammonium sulfate-precipitated nr-IGFBP-3 dose response in relative light units (RLU) from prototype CENTAUR® XP assay versus IMMULITE® value-assigned standards in an example, according to an embodiment consistent with the principles described herein. The graph is a master curve of the ammonium sulfate-precipitated BL7 standards that were value-assigned using the IMMULITE® 2000 predicate system.

TABLE 2

BL7 RLU S/N Ratios Using IMMULITE ®-Value Assigned Standards and Calibrators

| Name | RLU | Dose | S/N |
|---|---|---|---|
| BL7S01 | 11794 | 0 | 1.0 |
| BL7S02 | 114280 | 0.48 | 9.7 |
| BL7S03 | 217043 | 0.967 | 18.4 |
| BL7S04 | 435323 | 2.545 | 36.9 |
| BL7S05 | 799241 | 5.765 | 67.8 |
| BL7S06 | 1149399 | 11.45 | 97.5 |
| BL7S07 | 1463532 | 17.72 | 124.1 |
| BL7 Cal L | | 0.48 | |
| BL7 Cal H | | 11.00 | |

Dose values are in µg/ml.

The data of Table 2 and FIG. 4 show that ammonium sulfate salt, as a stronger anti-chaotropic agent than sodium sulfate, offers improved yields of precipitated nr-IGFBP-3 at a larger scale of starting BRT human serum. FIG. 4 shows the RLU values from Table 2 to a dose curve generated using the prototype ADVIA CENTAUR® IGFBP-3 assay. Using ammonium sulfate salt as the anti-chaotropic agent on a large scale amount of BRT human serum (1 liter or greater) allows for preparation of standards and calibrators (e.g., S06, S07 and High Calibrator BL7 Cal H) having much higher concentrations of nr-IGFBP-3 (i.e., 11.45 µg/ml, 17.72 µg/ml and 11.0 µg/ml, respectively) than nr-IGFBP-3 in the starting sample of BRT human serum (i.e. about 4.0-4.5 µg/ml) prior to the ammonium sulfate precipitation and filtration method (i.e., either ultrafiltration or TFF process).

It is also noted herein that the prototype ADVIA CENTAUR® IGFBP-3 assay provides dilution of human serum samples comprising unknown concentrations of nr-IGFBP-3 on the CENTAUR® systems with no manual dilutions. As such, an ability to generate standards, such as BL7S06 and BL7S07, the High Cal calibrator, and even high MDP samples, etc., this way allows a lab operator to handle nr-IGFBP-3 standards, calibrators, MDPs, etc., substantially the same way as the lab operator may handle unknown patient samples while covering substantially an entire working range of the pilot ADVIA CENTAUR® IGFBP-3 assay, for example.

Figure 5:
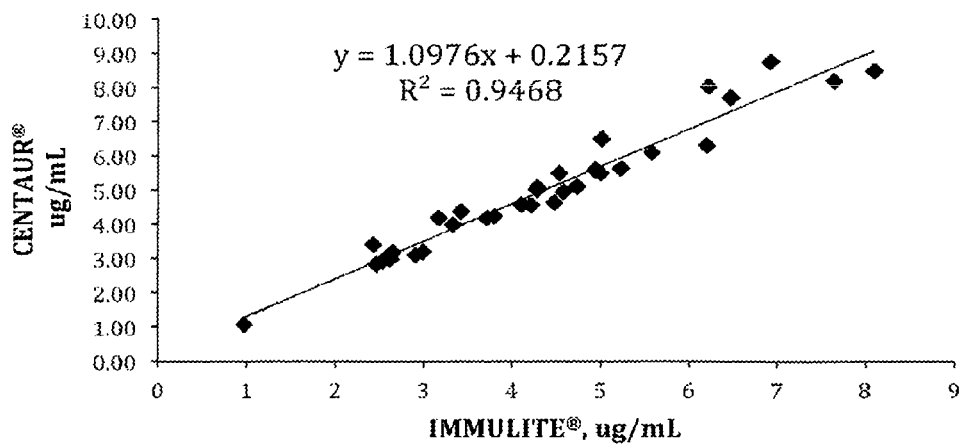
FIG. 5 illustrates a graph comparing dose values (full curve) for ammonium sulfate-precipitated nr-IGFBP-3 calibration standards from prototype CENTAUR® XP assay and IMMULITE® value-assigned standards in an example, according to an embodiment consistent with the principles described herein.
Figure 6:
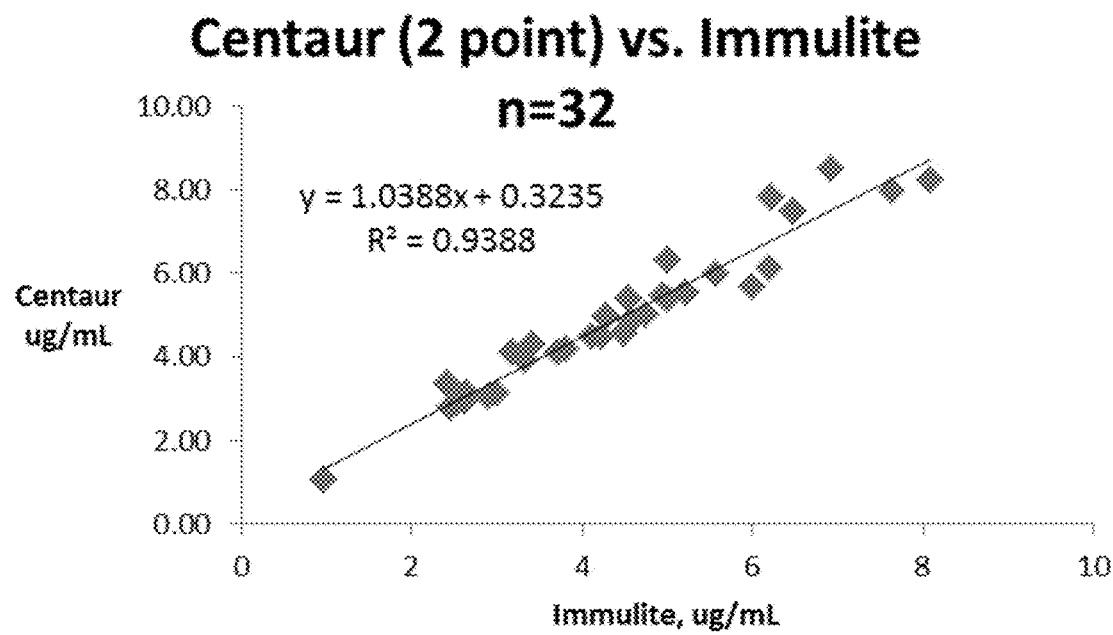
FIG. 6 illustrates a graph comparing dose values (2-point calculation) for ammonium sulfate-precipitated nr-IGFBP-3 calibration standards from prototype CENTAUR® XP assay and IMMULITE® value-assigned standards in an example, according to an embodiment consistent with the principles described herein.

FIGS. 5 and 6 illustrate method comparison data between CENTAUR® XP and IMMULITE® 2000 dose values, using a CENTAUR® full curve method and the 2-point data fitting calibration method, respectively. In particular, FIGS. 5 and 6 show method comparison data of the prototype ADVIA CENTAUR® IGFBP-3 assay as compared to the predicate device, IMMULITE® 2000 IGFBP-3 assay, when tested on the same samples of human serum comprising unknown concentrations of nr-IGFBP-3 (wherein the sample size is n=32 samples of human serum). For the prototype ADVIA CENTAUR® IGFBP-3 assay, concentration values of nr-IGFBP-3 were calculated using either a full-curve calculation (FIG. 5), or for FIG. 6, using a 2-point calibration using a Low calibrator (BL7 Cal L=0.48 µg/ml) and High calibrator (BL7 Cal H=11.00 µg/ml). The standards, BL7S01 to BL7S07, in FIGS. 5-6 were generated using ammonium sulfate as the anti-chaotropic precipitation agent and using ultrafiltration or a TFF process on BRT human serum.

Examples 3A-3B: Scale-Up of nr-IGFBP-3 Enrichment Using Ammonium Sulfate in a Sodium Phosphate Solution Saturated ammonium sulfate solution was mixed with equal volume of BRT1 serum for the precipitation. The process was scaled up from 100 ml to 1000 ml human serum. A sodium phosphate aqueous solution (about 50-52 mM) was used for the saturated ammonium sulfate solution. Table 3 summarizes yields based on the prototype CENTAUR® IGFBP-3 binding assay. One liter each of BRT1 human serum was processed with different equipment, as described below for Example 3A and Example 3B.

Example 3A

The human serum was handled using the equipment described in Example 1 above.

Example 3B

The human serum was precipitated by 50% saturated ammonium sulfate in sodium phosphate solution and was centrifuged using an ADVANTI™ Centrifuge model J-20XPI from Beckman Coulter; and the buffer exchange into PBS/sodium azide was done by a Tangential Flow Filter (TFF) by Scilog, equipped with a TFF cassette (cat no. OS030T12) from Pall Corporation, Port Washington, NY. Final reduction of about 800 ml down to 200 ml was done on an AMICON® Stirred Cell. A detailed summary of yields from Examples 1, 2 and 3A-B are summarized in Table 3.

Table 3 shows that the prototype CENTAUR® IGFBP-3 binding assay is configured to support larger scale batch size processing with consistent or increasing higher percent yield of nr-IGFBP-3 (Examples 3A-3B at 1000 ml BRT volume). Further, Table 3 shows that the stronger anti-chaotropic agent, i.e., ammonium sulfate, used for precipitating the nr-IGFBP-3, produced higher yields than did the sodium sulfate, was compatible with the larger scale processing, and performed well (to precipitate out the nr-IGFBP-3) whether mixed in water or mixed a solution of sodium phosphate in water and filtered/buffer exchanged using an ultrafiltration system or TFF system. The yield of nr-IGFBP-3 was highest in Example 3B, that used ammonium sulfate in a sodium phosphate solution with 1 liter of human serum (1:1 ratio) for precipitation and TFF system for separation, buffer exchange and concentration of the nr-IGFBP-3.

TABLE 3

Percent Yields After Sodium Sulfate and Ammonium Sulfate Precipitation

| Examples | BRT1 Vol. (ml) | Precipitated by | Solvent/Buffer | BRT1 Input, (µg) | Yield, (µg) | % Yield |
|---|---|---|---|---|---|---|
| 1 | 200 | Sodium Sulfate | Water | 900 | 423 | 47% |
| 2A | 200 | Ammonium Sulfate | Water | 784 | 538 | 69% |
| 2B | 400 | Ammonium Sulfate | Water | 1568 | 1136 | 72% |
| 3A | 1000 | Ammonium Sulfate | 51 mM sodium phosphate, pH 7.4 | 5480 | 4055 | 74% |
| 3B | 1000 | Ammonium Sulfate | 52 mM sodium phosphate, pH 7.4 | 5480 | 4165 | 76% |

Example 4: nr-IGFBP-3 Purification and Enrichment Using Hydrophobic Interaction Chromatography (HIC)

Example 4 was carried out using a porous matrix of sepharose-based resin in a HIC chromatography column using Phenyl Sepharose 6FF. Twenty five ml of Phenyl Sepharose 6FF (GE Life Sciences, Marlborough, MA, cat no. 17-0973-10) in 20% ethanol was exchanged into water in a glass funnel then packed into an XK16/20 column (GE Life Sciences, cat no. 28-988937) and the gel was equilibrated with 100 ml of Buffer A: 25 mM Tris (pH 8.1) with 0.35 M ammonium sulfate buffer (pH 8.1) (i.e., the 'second buffer solution', described above). Twenty five ml of Highly normalized human serum (BRT1, Bioresource Technology, cat no. H1090, lot no. 1407033) were filtered to a 0.2 micron filter and mixed with 25 ml of Buffer B: 50 mM Tris (pH 8.1), 0.7 M ammonium sulfate buffer (i.e., the 'first buffer solution', described above) at room temperature for 10 min. The 50 ml serum mixture was applied to the column at about 3 ml/min and the unbound fraction was washed with 100 ml of Buffer A. One hundred ml of Buffer C: 25 mM Tris (pH 8.1) (i.e., the 'third buffer solution', described above) was then applied to elute the bound nr-IGBBP3.

An amount of 280 ml of the input BRT1, diluted 1:100 in Buffer C, and 1:10 dilution of unbound and eluted fractions in Buffer C were measured by a UV-VIS Spectrophotometer and doses of nr-IGFBP-3 (in µg/ml) were measured by the CENTAUR® IGFBP-3 prototype assay. The eluted fraction was further buffer exchanged into PBS/0.09% sodium azide by an AMICON® Stirred Cell equipped with a continuous flow mini reservoir. Finally, the volume of the buffer-exchanged nr-IGFBP-3 was reduced to 10 ml.

A total of 103.6 µg of nr-IGFBP-3 was eluted from the Phenyl Sepharose 6FF from a total of 116.75 µg of input nr-IGFBP-3. The percent (%) yield from HIC chromatography using the Phenyl Sepharose 6FF, after buffer exchange, was 89%. The vendor Instructions 71-5002-39 AC from GE Healthcare Life Sciences were followed to regenerate the Phenyl Sepharose.

Example 5: Environmental/Temperature Impact Using Recombinant Human IGFBP-3 Studies Using Recombinant Human IGFBP-3 as Calibration Standards An immunoassay method is expected to deliver reliable results under normal laboratory conditions of 24° C. plus or minus 6° C. Bias was calculated by dividing the difference of high dose and the low dose values with the dose value at 18° C., 24° C. and 30° C. A typical specification was set, for example, that the bias should not be greater than 10% for an individual sample or 15% for the average of several samples. Tables 4, 5 and 6 summarize the bias tables for IGFBP-3 assays of nr-IGFPB-3 samples ('BL5U') prepared according to Example 1 herein, BRT1 (cat. no. H1090, lot no. 1407033, highly normalized human serum from Bioresources Technology, Inc.), and of samples using commercial recombinant IGFBP-3 (r-IGFBP-3) from R and D Systems, Inc., Minneapolis, MN, (cat. no. 675-B3-025) and Peprotech, Rocky Hill, NJ, (cat. no. 100-08), using full curve analysis at 18° C., 24° C. and 30° C. stored curves, respectively.

Tables 5-7 show that in many instances, the r-IGFBP-3 samples from R and D Systems and Peprotech are over-recovered in a target range of at least about 4 µg/ml and greater compared to the nr-IGFBP-3 in the BRT1 and BL5U samples.

TABLE 5

CENTAUR ® XP Environment Impact Table of nr-IGFBP-3 Samples ('BL5U'),
BRT1 Human Serum and R-IGFBP-3 Samples From R & D Systems ('Rndbrtee2'),
and Peprotech ('Pepbrtee2') Full Curve Analysis Using Stored Curve at 18° C.

| Sample | 18° C. AF10015B Dose | 24° C. AF09915A Dose | 30° C. AF10315A Dose | Highest Dose | Lowest Dose | % Bias |
|---|---|---|---|---|---|---|
| BL5US01 | 0.00 | . | 0.00 | 0.00 | 0.00 | |
| BL5US02 | 0.44 | 0.41 | 0.47 | 0.47 | 0.41 | 13.5% |
| BL5US03 | 0.86 | 0.84 | 0.93 | 0.93 | 0.84 | 11.5% |
| BL5US04 | 2.51 | 2.49 | 2.75 | 2.75 | 2.49 | 10.6% |
| BL5US05 | 5.36 | 5.40 | 5.91 | 5.91 | 5.36 | 10.3% |
| BL5US06 | 9.72 | 9.31 | 10.80 | 10.80 | 9.31 | 16.0% |
| BL5US07 | 16.07 | 16.07 | 17.64 | 17.64 | 16.07 | 9.8% |
| BL5L01 | 0.43 | 0.40 | 0.45 | 0.45 | 0.40 | 12.8% |
| BL5H01 | 9.96 | 9.88 | 11.09 | 11.09 | 9.88 | 12.3% |
| BRT1 | 4.57 | 4.75 | 5.17 | 5.17 | 4.57 | 12.6% |

| Target | | 18° C. | 24° C. | 30° C. | | |
|---|---|---|---|---|---|---|
| | Peprotech r-IGFBP3 | | | | | |
| 1 μg/mL | PepBRTeE2_01 | 2.55 | 2.40 | 2.60 | 2.60 | 2.40 | 8.3% |
| 4 μg/mL | PepBRTeE2_04 | 14.94 | 13.41 | 15.65 | 15.65 | 13.41 | 16.7% |
| 8 μg/mL | PepBRTeE2_08 | 56.89 | 45.62 | 61.13 | | | |
| 12 μg/mL | PepBRTeE2_12 | 238.25 | 141.03 | 197.25 | | | |
| | RnD Systems r-IGFBP3 | | | | | |
| 1 μg/mL | RnDBRTeE2_01 | 1.12 | 1.04 | 1.17 | 1.17 | 1.04 | 12.0% |
| 4 μg/mL | RnDBRTeE2_04 | 5.26 | 4.81 | 5.63 | 5.63 | 4.81 | 17.1% |
| 8 μg/mL | RnDBRTeE2_08 | 12.53 | 11.42 | 13.91 | 13.91 | 11.42 | 21.9% |
| 12 μg/mL | RnDBRTeE2_12 | 23.22 | 19.25 | 24.25 | | | |

TABLE 6

CENTAUR ® XP Environment Impact Table of nr-IGFBP-3 Samples ('BL5U'),
BRT1 Human Serum and R-IGFBP-3 Samples From R & D Systems ('Rndbrtee2'),
and Peprotech ('Pepbrtee2') Full Curve Analysis Using Stored Curve at 24° C.

| Sample | 18° C. AF10015B Dose | 24° C. AF09915A Dose | 30° C. AF10315A Dose | Highest Dose | Lowest Dose | % Bias |
|---|---|---|---|---|---|---|
| BL5US01 | 0.02 | 0.00 | 0.02 | 0.02 | 0.00 | |
| BL5US02 | 0.46 | 0.44 | 0.49 | 0.49 | 0.44 | 12.8% |
| BL5US03 | 0.89 | 0.86 | 0.96 | 0.96 | 0.86 | 11.2% |
| BL5US04 | 2.54 | 2.52 | 2.78 | 2.78 | 2.52 | 10.6% |
| BL5US05 | 5.41 | 5.45 | 5.98 | 5.98 | 5.41 | 10.3% |
| BL5US06 | 9.85 | 9.43 | 10.96 | 10.96 | 9.43 | 16.2% |
| BL5US07 | 16.41 | 16.41 | 18.05 | 18.05 | 16.41 | 10.0% |
| BL5L01 | 0.45 | 0.42 | 0.47 | 0.47 | 0.42 | 12.1% |
| BL5H01 | 10.10 | 10.01 | 11.26 | 11.26 | 10.01 | 12.5% |
| BRT1 | 4.62 | 4.80 | 5.22 | 5.22 | 4.62 | 12.6% |

| Target | | 18° C. | 24° C. | 30° C. | | |
|---|---|---|---|---|---|---|
| | Peprotech r-IGFBP3 | | | | | |
| 1 μg/mL | PepBRTeE2_01 | 2.58 | 2.43 | 2.63 | 2.63 | 2.43 | 8.2% |
| 4 μg/mL | PepBRTeE2_04 | 15.23 | 13.65 | 15.97 | 15.97 | 13.65 | 17.0% |
| 8 μg/mL | PepBRTeE2_08 | 61.06 | 48.29 | 65.94 | | | |
| 12 μg/mL | PepBRTeE2_12 | 320.26 | 167.79 | 251.21 | | | |
| | RnD Systems r-IGFBP3 | | | | | |
| 1 μg/mL | RnDBRTeE2_01 | 1.15 | 1.07 | 1.19 | 1.19 | 1.07 | 11.7% |
| 4 μg/mL | RnDBRTeE2_04 | 5.31 | 4.86 | 5.69 | 5.69 | 4.86 | 17.1% |
| 8 μg/mL | RnDBRTeE2_08 | 12.75 | 11.59 | 14.17 | 14.17 | 11.59 | 22.2% |
| 12 μg/mL | RnDBRTeE2_12 | 23.92 | 19.73 | 25.01 | | | |

TABLE 7

CENTAUR ® XP Environment Impact Table of nr-IGFBP-3 Samples ('BL5U'),
BRT1 Human Serum and R-IGFBP-3 Samples From R & D Systems ('Rndbrtee2'),
and Peprotech ('Pepbrtee2') Full Curve Analysis Using Stored Curve at 30° C.

| Sample | 18° C. AF10015B Dose | 24° C. AF09915A Dose | 30° C. AF10315A Dose | Highest Dose | Lowest Dose | % Bias |
|---|---|---|---|---|---|---|
| BL5US01 | 0.00 | . | 0.00 | 0.00 | 0.00 | |
| BL5US02 | 0.41 | 0.39 | 0.44 | 0.44 | 0.39 | 13.3% |
| BL5US03 | 0.80 | 0.78 | 0.86 | 0.86 | 0.78 | 11.3% |
| BL5US04 | 2.29 | 2.27 | 2.51 | 2.51 | 2.27 | 10.5% |
| BL5US05 | 4.86 | 4.89 | 5.36 | 5.36 | 4.86 | 10.2% |
| BL5US06 | 8.79 | 8.42 | 9.77 | 9.77 | 8.42 | 16.1% |
| BL5US07 | 14.57 | 14.57 | 16.01 | 16.01 | 14.57 | 9.9% |
| BL5L01 | 0.40 | 0.37 | 0.42 | 0.42 | 0.37 | 12.6% |
| BL5H01 | 9.01 | 8.93 | 10.03 | 10.03 | 8.93 | 12.3% |
| BRT1 | 4.15 | 4.31 | 4.68 | 4.68 | 4.15 | 12.4% |
| Target | | 18° C. | 24° C. | 30° C. | | |
| Peprotech r-IGFBP3 | | | | | | |
| 1 µg/mL PepBRTeE2_01 | | 2.33 | 2.19 | 2.37 | 2.37 2.19 | 8.2% |
| 4 µg/mL PepBRTeE2_04 | | 13.53 | 12.14 | 14.18 | 14.18 12.14 | 16.8% |
| 8 µg/mL PepBRTeE2_08 | | 53.93 | 42.63 | 58.25 | | |
| 12 µg/mL PepBRTeE2_12 | | 298.98 | 150.92 | 230.31 | | |
| RnD Systems r-IGFBP3 | | | | | | |
| 1 µg/mL RnDBRTeE2_01 | | 1.04 | 0.96 | 1.08 | 1.08 0.96 | 11.8% |
| 4 µg/mL RnDBRTeE2_04 | | 4.76 | 4.36 | 5.10 | 5.10 4.36 | 16.9% |
| 8 µg/mL RnDBRTeE2_08 | | 11.34 | 10.32 | 12.60 | 12.60 10.32 | 22.0% |
| 12 µg/mL RnDBRTeE2_12 | | 21.17 | 17.48 | 22.13 | | |

Studies Using Sodium or Ammonium Sulfate Precipitated Calibration Standards:

As a comparison, the temperature sensitivity studies of BL5U standards (prepared using procedure in Example 1) and BL6 standards (ammonium sulfate-precipitated nr-IGFBP-3), and sample recovery using the standards at 18° C., 24° C. and 30° C. using CENTAUR® XP System ED are summarized in Tables 8, 9 and 10 along with patient samples ('GALO') and IMMULITE® assay control samples ('Imm0028K').

TABLE 8

CENTAUR ® XP System ED Environment Impact
Table Using BL5U Calibrators, BL6 Calibrators, Patient
Samples, and IMMULITE ® Control Samples
with Master Curve Stored Curve at 18° C.

| | Centaur ED Stored 18° C. | | | | | |
|---|---|---|---|---|---|---|
| Sample | 18° C. Dose | 24° C. Dose | 30° C. Dose | Max | Min | % Bias |
| BL5US01 | NA | NA | NA | NA | NA | NA |
| BL5US02 | 0.37 | 0.33 | 0.33 | 0.37 | 0.33 | 14% |
| BL5US03 | 0.74 | 0.69 | 0.70 | 0.74 | 0.69 | 6% |
| BL5US04 | 2.17 | 2.13 | 2.20 | 2.20 | 2.13 | 3% |
| BL5US05 | 4.65 | 4.62 | 4.95 | 4.95 | 4.62 | 7% |
| BL5US06 | 8.93 | 8.83 | 9.24 | 9.24 | 8.83 | 5% |
| BL5US07 | 15.12 | 15.06 | 16.08 | 16.08 | 15.06 | 7% |
| BL5L01 | 0.37 | 0.32 | 0.32 | 0.37 | 0.32 | 14% |
| BL5H01 | 8.78 | 8.61 | 9.56 | 9.56 | 8.61 | 11% |
| BL6S01 | NA | NA | NA | NA | NA | NA |
| BL6S02 | 0.34 | 0.30 | 0.28 | 0.34 | 0.28 | 19% |
| BL6S03 | 0.73 | 0.67 | 0.66 | 0.73 | 0.66 | 10% |
| BL6S04 | 2.02 | 1.96 | 2.08 | 2.08 | 1.96 | 6% |
| BL6S05 | 4.56 | 4.37 | 4.81 | 4.81 | 4.37 | 10% |
| BL6S06 | 9.43 | 9.29 | 9.40 | 9.43 | 9.29 | 2% |
| BL6S07 | 16.62 | 16.59 | 16.79 | 16.79 | 16.59 | 1% |

TABLE 8-continued

CENTAUR ® XP System ED Environment Impact
Table Using BL5U Calibrators, BL6 Calibrators, Patient
Samples, and IMMULITE ® Control Samples
with Master Curve Stored Curve at 18° C.

| | Centaur ED Stored 18° C. | | | | | |
|---|---|---|---|---|---|---|
| Sample | 18° C. Dose | 24° C. Dose | 30° C. Dose | Max | Min | % Bias |
| BL6L01 | 0.36 | 0.30 | 0.28 | 0.36 | 0.28 | 25% |
| BL6H01 | 9.73 | 9.09 | 9.41 | 9.73 | 9.09 | 7% |
| Imm0028K1 | 0.91 | 0.86 | 0.89 | 0.91 | 0.86 | 5% |
| Imm0028K2 | 3.73 | 3.68 | 3.87 | 3.87 | 3.68 | 5% |
| GAL026 | 2.47 | 2.49 | 2.56 | 2.56 | 2.47 | 3% |
| GAL028 | 4.39 | 4.30 | 4.57 | 4.57 | 4.30 | 6% |
| GAL029 | 5.38 | 5.39 | 5.68 | 5.68 | 5.38 | 5% |
| GAL036 | 4.56 | 4.58 | 4.61 | 4.61 | 4.56 | 1% |
| GAL038 | 4.38 | 4.27 | 4.37 | 4.38 | 4.27 | 3% |
| GAL039 | 2.81 | 2.77 | 2.83 | 2.83 | 2.77 | 2% |
| GAL040 | 4.14 | 4.03 | 4.39 | 4.39 | 4.03 | 9% |
| GAL041 | 3.88 | 4.01 | 4.14 | 4.14 | 3.88 | 7% |
| GAL042 | 3.67 | 3.63 | 3.83 | 3.83 | 3.63 | 5% |
| GAL043 | 2.53 | 2.56 | 2.68 | 2.68 | 2.53 | 6% |
| GAL044 | 4.06 | 4.18 | 4.43 | 4.43 | 4.06 | 9% |
| GAL045 | 4.41 | 4.34 | 4.56 | 4.56 | 4.34 | 5% |

TABLE 9

CENTAUR® XP System ED Environment Impact Table Using BL5U Calibrators, BL6 Calibrators, Patient Samples, and IMMULITE® Control Samples with Master Curve Stored Curve at 24° C.

| | Centaur ED Stored 24° C. | | | | | |
|---|---|---|---|---|---|---|
| Sample | 18° C. Dose | 24° C. Dose | 30° C. Dose | Max | Min | % Bias |
| BL5US01 | NA | NA | NA | NA | NA | NA% |
| BL5US02 | 0.41 | 0.37 | 0.37 | 0.41 | 0.37 | 13% |
| BL5US03 | 0.78 | 0.74 | 0.75 | 0.78 | 0.74 | 6% |
| BL5US04 | 2.21 | 2.18 | 2.24 | 2.24 | 2.18 | 3% |
| BL5US05 | 4.70 | 4.67 | 5.00 | 5.00 | 4.67 | 7% |
| BL5US06 | 9.00 | 8.90 | 9.30 | 9.30 | 8.90 | 5% |
| BL5US07 | 15.19 | 15.13 | 16.15 | 16.15 | 15.13 | 7% |
| BL5L01 | 0.41 | 0.36 | 0.36 | 0.41 | 0.36 | 13% |
| BL5H01 | 8.85 | 8.67 | 9.62 | 9.62 | 8.67 | 11% |
| BL6S01 | NA | NA | NA | NA | NA | NA |
| BL6S02 | 0.38 | 0.34 | 0.32 | 0.38 | 0.32 | 17% |
| BL6S03 | 0.77 | 0.72 | 0.70 | 0.77 | 0.70 | 9% |
| BL6S04 | 2.06 | 2.00 | 2.12 | 2.12 | 2.00 | 6% |
| BL6S05 | 4.61 | 4.42 | 4.86 | 4.86 | 4.42 | 10% |
| BL6S06 | 9.50 | 9.35 | 9.47 | 9.50 | 9.35 | 2% |
| BL6S07 | 16.70 | 16.67 | 16.87 | 16.87 | 16.67 | 1% |
| BL6L01 | 0.40 | 0.34 | 0.32 | 0.40 | 0.32 | 23% |
| BL6H01 | 9.80 | 9.15 | 9.47 | 9.80 | 9.15 | 7% |
| Imm0028K1 | 0.95 | 0.91 | 0.93 | 0.95 | 0.91 | 5% |
| Imm0028K2 | 3.78 | 3.73 | 3.92 | 3.92 | 3.73 | 5% |
| GAL026 | 2.52 | 2.53 | 2.60 | 2.60 | 2.52 | 3% |
| GAL028 | 4.44 | 4.35 | 4.62 | 4.62 | 4.35 | 6% |
| GAL029 | 5.44 | 5.44 | 5.73 | 5.73 | 5.44 | 5% |
| GAL036 | 4.61 | 4.63 | 4.66 | 4.66 | 4.61 | 1% |
| GAL038 | 4.43 | 4.32 | 4.42 | 4.43 | 4.32 | 3% |
| GAL039 | 2.85 | 2.81 | 2.87 | 2.87 | 2.81 | 2% |
| GAL040 | 4.19 | 4.08 | 4.44 | 4.44 | 4.08 | 9% |
| GAL041 | 3.93 | 4.06 | 4.19 | 4.19 | 3.93 | 7% |
| GAL042 | 3.71 | 3.68 | 3.88 | 3.88 | 3.68 | 5% |
| GAL043 | 2.58 | 2.60 | 2.73 | 2.73 | 2.58 | 6% |
| GAL044 | 4.11 | 4.23 | 4.48 | 4.48 | 4.11 | 9% |
| GAL045 | 4.46 | 4.39 | 4.61 | 4.61 | 4.39 | 5% |

TABLE 10

CENTAUR® XP System ED Environment Impact Table Using BL5U Calibrators, BL6 Calibrators, Patient Samples, and IMMULITE® Control Samples with Master Curve Stored Curve at 30° C.

| | Centaur ED Stored 30° C. | | | | | |
|---|---|---|---|---|---|---|
| Sample | 18° C. Dose | 24° C. Dose | 30° C. Dose | Max | Min | % Bias |
| BL5US01 | NA | NA | NA | NA | NA | NA |
| BL5US02 | 0.42 | 0.38 | 0.37 | 0.42 | 0.37 | 12% |
| BL5US03 | 0.77 | 0.73 | 0.74 | 0.77 | 0.73 | 6% |
| BL5US04 | 2.13 | 2.10 | 2.16 | 2.16 | 2.10 | 3% |
| BL5US05 | 4.48 | 4.45 | 4.76 | 4.76 | 4.45 | 7% |
| BL5US06 | 8.50 | 8.41 | 8.79 | 8.79 | 8.41 | 4% |
| BL5US07 | 14.28 | 14.23 | 15.18 | 15.18 | 14.23 | 7% |
| BL5L01 | 0.41 | 0.37 | 0.37 | 0.41 | 0.37 | 12% |
| BL5H01 | 8.36 | 8.20 | 9.09 | 9.09 | 8.20 | 11% |
| BL6S01 | NA | NA | NA | NA | NA | NA |
| BL6S02 | 0.38 | 0.35 | 0.33 | 0.38 | 0.33 | 16% |
| BL6S03 | 0.76 | 0.71 | 0.69 | 0.76 | 0.69 | 9% |
| BL6S04 | 1.99 | 1.93 | 2.05 | 2.05 | 1.93 | 6% |
| BL6S05 | 4.39 | 4.21 | 4.63 | 4.63 | 4.21 | 10% |
| BL6S06 | 8.97 | 8.83 | 8.94 | 8.97 | 8.83 | 2% |
| BL6S07 | 15.69 | 15.66 | 15.85 | 15.85 | 15.66 | 1% |
| BL6L01 | 0.40 | 0.34 | 0.33 | 0.40 | 0.33 | 21% |
| BL6H01 | 9.25 | 8.65 | 8.95 | 9.25 | 8.65 | 7% |
| Imm0028K1 | 0.93 | 0.89 | 0.91 | 0.93 | 0.89 | 5% |
| Imm0028K2 | 3.61 | 3.56 | 3.74 | 3.74 | 3.56 | 5% |
| GAL026 | 2.42 | 2.43 | 2.50 | 2.50 | 2.42 | 3% |
| GAL028 | 4.23 | 4.15 | 4.40 | 4.40 | 4.15 | 6% |
| GAL029 | 5.17 | 5.17 | 5.45 | 5.45 | 5.17 | 5% |
| GAL036 | 4.40 | 4.41 | 4.44 | 4.44 | 4.40 | 1% |
| GAL038 | 4.22 | 4.12 | 4.22 | 4.22 | 4.12 | 2% |
| GAL039 | 2.74 | 2.70 | 2.75 | 2.75 | 2.70 | 2% |
| GAL040 | 4.00 | 3.89 | 4.24 | 4.24 | 3.89 | 9% |
| GAL041 | 3.75 | 3.88 | 4.00 | 4.00 | 3.75 | 6% |
| GAL042 | 3.55 | 3.52 | 3.70 | 3.70 | 3.52 | 5% |
| GAL043 | 2.48 | 2.50 | 2.62 | 2.62 | 2.48 | 6% |
| GAL044 | 3.92 | 4.04 | 4.27 | 4.27 | 3.92 | 9% |
| GAL045 | 4.25 | 4.18 | 4.39 | 4.39 | 4.18 | 7% |

Example 6: Building of IGF-1 Standards Using Ammonium Sulfate Precipitated nr-IGFBP-3 Calibration Standards The molecular weight (about 150,000) of the nr-IGFBP-3 complex comprises IGF binding protein 3 bound with IGF-1 and/or IGF-2 plus the acid labile segments (ALS). The measurement of nr-IGFBP-3 analyte levels is applicable to the measurement of IGF-1 analyte levels using the IGF binding protein stock solution and the nr-IGFBP-3 calibration standards described herein. The nr-IGFBP-3 and IGF-1 levels for BL7 standards from Example 2 on IMMULITE® 2000 are summarized in Table 11.

TABLE 11

Doses of nr-IGFBP-3 and IGF-1 Measured by IMMULITE® 2000

| Sample | nr-IGFBP-3 (µg/ml) | IGF-1 (ng/ml) |
|---|---|---|
| BL7S01 | 0 | 24.2 |
| BL7S02 | 0.48 | 36.2 |
| BL7S03 | 0.967 | 51.4 |
| BL7S04 | 2.545 | 84.8 |
| BL7S05 | 5.765 | 141 |
| BL7S06 | 11.45 | 226 |
| BL7S07 | 17.72 | 363 |

Method of Preparing Human Serum that is Substantially-free of IGF Binding Protein

Example 7: Acid-Treated Charcoal Adsorbed (ATCA) Human Serum

Highly Normalized Serum (BRT1) from Bioresource Technology, cat no. H1090, lot no. 1407033 was filtered to a 0.2 µm filter and to which 0.375 g glycine (Sigma G7407, molecular weight equal to 75.07) was added. The solution was mixed with a magnetic stirrer and the pH of the solution containing 25 mM glycine was slowly adjusted down to pH 3.0 plus or minus pH 0.1 with 5N HCl, mixed at slow speed and maintained at the pH range for 2 hours at room temperature. Meanwhile, a Millipore MILLISTAK+® Pod charcoal cartridge, cat no. MCR40027H1 with a surface area of 270 square centimeters (cm$^2$) was flushed with 2 liters of deionized water. The water trapped in the cartridge was then blown dry by filtered house air.

The acid-treated serum was then loaded to the charcoal cartridge at a speed of 2-3 ml/min using a MASTERFLEX® C/L pump, model 77122-24, for example from Cole-Palmer, IL. The effluent (unbound fraction) was collected as Fraction 1. Two hundred ml of water was then pumped through and collected as Fraction 2 and the process was repeated by pumping through 200 ml water and the eluent was collected as Fraction 3. The input BRT1 as well as Fractions 1, 2 and 3 of the acid treated, charcoal absorbed (ATCA) BRT1 were read on a Varian CARY® 50 Conc UV Spectrophotometer from Agilent Technologies, CA, and assayed on a CENTAUR® XP.

Figure 7:
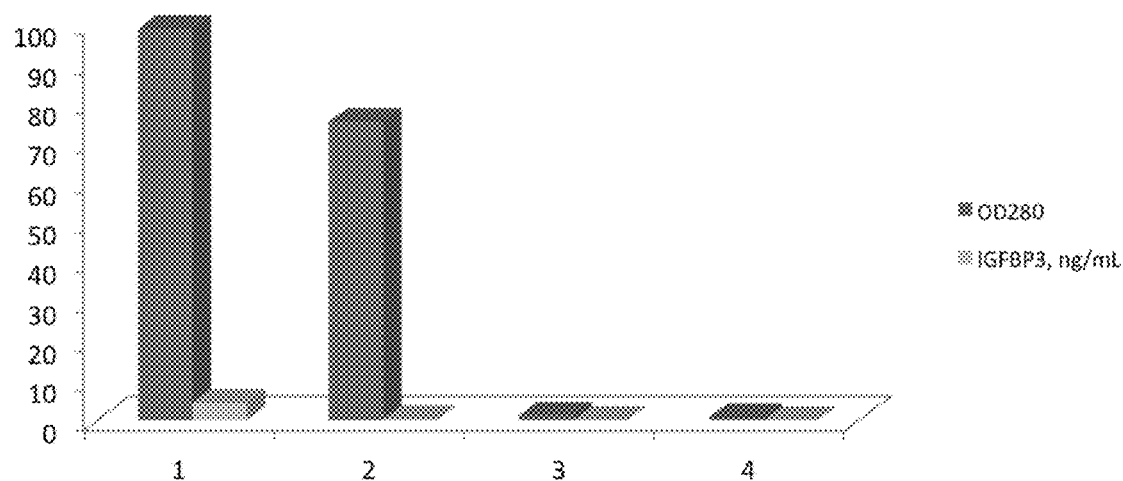
FIG. 7 illustrates a bar graph of elution profiles of serum proteins ('OD280') and nr-IGFBP-3 from acid treated, charcoal absorbed human serum in an example, according to an embodiment consistent with the principles described herein.

FIG. 7 and Table 12 show optical density at 280 nanometers (nm) ('OD280') and amount of IGFBP-3 (µg/ml) from the elution fractions of ATCA BRT1. The OD280 values accounted for the dilution factor with no interference from non-protein component after dilution. Column labeled 'A280' is protein absorption at 280 nm, which provides a way to quantify protein in solution. The Fractions 1 and 2 were combined, concentrated to 200 ml then buffer-exchanged into PBS/0.9% sodium azide by an AMICON® Stirred Cell, EMD Millipore Corp., using 1000 ml of the PBS/0.9% sodium azide buffer. Several assays were conducted with the combined and buffer-exchanged Fractions 1 and 2 of the acid-treated charcoal adsorbed sample ('ATCA-3') of the human serum and the results of the assays are summarized in Table 13.

Table 13 provides endogenous levels of IGFBP-3, IGF-1, and hGH (human Growth Hormone) in BRT1 prior to processing that were determined by analysis using Siemens assays (on either IMMULITE® or CENTAUR® systems) and compared with levels determined after processing.

Example 8: Scale-Up Preparations of Acid-Treated Charcoal Adsorbed (ATCA) Human Serum Four hundred ml of BRT1 human serum was processed the same way as mentioned in Example 7, the unbound fraction to the charcoal cartridge (about 380 ml) was collected and pH of the stripped serum was immediately adjusted to pH 7.4 plus or minus pH 0.05 with 5 N HCl, but unlike the Example 7, the fractions washed by water were discarded. The unbound fraction of the ATCA serum in this Example ('ATCA-4') was then buffer exchanged into PBS/0.9% sodium azide by an AMICON® Stirred Cell using 5 times the volume of the buffer or a MINIMATE™ TFF System from Pall Corporation, equipped with a 10 KDa molecular weight membrane.

Regeneration of Charcoal Cartridge:

In order to test the capacity of the Millipore charcoal cartridge, the process was repeated once more with 400 ml BRT1 human serum to make an ATCA sample ('ATCA-5') of human serum which was found to saturate the charcoal cartridge and resulted in 1.44 µg/ml IGFBP-3. The mitigation of the preparation was done by a regeneration of the charcoal cartridge using 0.5N NaOH in 20% ethanol, similar to a procedure described in U.S. Patent Application Publication No. 20080286193A1, incorporated herein by reference, then wash extensively with water. To the ATCA-5 serum was added 25 mM glycine and pH was adjusted down to pH 3.0 plus or minus (+/−) 0.1 and mixed at room temperature for 2 hours. The acid-treated serum was then loaded to the regenerated charcoal cartridge and an unbound fraction (about 360 ml) was collected ('ATCA-5A'). After a buffer exchange into PBS/0.09% sodium azide, the IGFBP-3 dose of the ATCA-5A was determined by a prototype CENTAUR® Assay. Table 14 summarizes the results of the 3 preparations according to Examples 7-8 and sample ATCA-5A.

TABLE 12

OD280 and IGFBP3 Doses for the Elution Factions from Charcoal Cartridge

| | A280 | Dilution factor | OD280 | IGFBP-3 (µg/ml) |
|---|---|---|---|---|
| Input | 0.9874 | 100 | 98.74 | 4.49 |
| Fraction 1 | 0.7522 | 100 | 75.22 | 0.19 |
| Fraction 2 | 0.1174 | 10 | 1.174 | 0.01 |
| Fraction 3 | 0.072 | 10 | 0.72 | 0.00 |

TABLE 13

Dose Summary of Various CENTAUR ® Assays for BRT1 and ATCA-3 Human Serum

| Sample No. | Analyte | Binding Protein | ATCA3 Dose (µg/ml) | BRT Dose | % Depleted | Instrument |
|---|---|---|---|---|---|---|
| 1 | IGFBP3 | NA | <0.5 | 4.36 µg/ml | >90% | IMMULITE ® 2000 |
| 2 | IGFBP3 | NA | 0.17 | 4.37 µg/ml | 96.1% | CENTAUR ® XP |
| 3 | IGF1 | IGFBP3 | 3.98 | 110 ng/ml | 96.4% | IMMULITE ® 2000 |
| 4 | hGH | hGHBP | 0.1 | 0.63 µg/ml | 84.1% | CENTAUR ® XP |

For Sample No. 1: The analytical sensitivity was equal to 0.1 µg/ml.
For Sample No. 2: The LOQ was undetermined.
For Sample No. 3: The analytical sensitivity was equal to 20 ng/ml.
For Sample No. 4: The analytical sensitivity was equal to 0.1 µg/ml.

TABLE 14

A summary of ATCA Human Serum Preparation

| Material | Starting BRT1 (ml) | IGFBP-3 (µg/ml) |
|---|---|---|
| ATCA-3 | 200 | 0.17 |
| ATCA-4 | 400 | 0.36 |
| ATCA-5 | 400 | 1.44 |
| ATCA-5A* | 380* | 0.17 |

*Used the ATCA-5, acid-treated again and passed to a regenerated charcoal cartridge Example 9: IGFBP-3 Patient Sample Dilution Recovery A ProMedDx (Norton, MA) Sample ID 10476627, pediatric serum sample (ages 14-16), with IGFBP-3 dose at 7.76 µg/ml on IMMULITE® 2000 and CENTAUR® dose at 7.39 µg/ml was subjected to dilutions in the ATCA-5A human serum and run on a prototype IGFBP-3 test on a CENTAUR® XP according to Table 15 for diluted sample preparation where doses measured and calculated are also provided.

Table 15 provides a dilution series using ATCA-5A as diluent and the pediatric sample. The dilution series was accomplished in the following manner: IGFPB-3 values for P1 (ATCA-5) and P7 (undiluted Pediatric sample) were measured in the prototype CENTAUR® IGFBP-3 assay. Samples P1 & P7 were mixed in equal amounts (1:1) to make Sample P4; Samples P1 & P4 were mixed 1:1 to make Sample P3; Samples P1 & P3 were mixed 1:1 to make Sample P2; Samples P3 & P7 were mixed 1:1 to make Sample P5; and Samples P5 & P7 were mixed 1:1 to make Sample P6. The calculated dose was the mathematical dose expected from the mixing (for example, for Sample P4 the calculated dose is equal to P1+P7 (i.e., 0.15+7.39=7.54) divided by 2=3.77. The measured dose is what was determined by testing in the prototype IGFBP-3 CENTAUR® assay.

Figure 8:
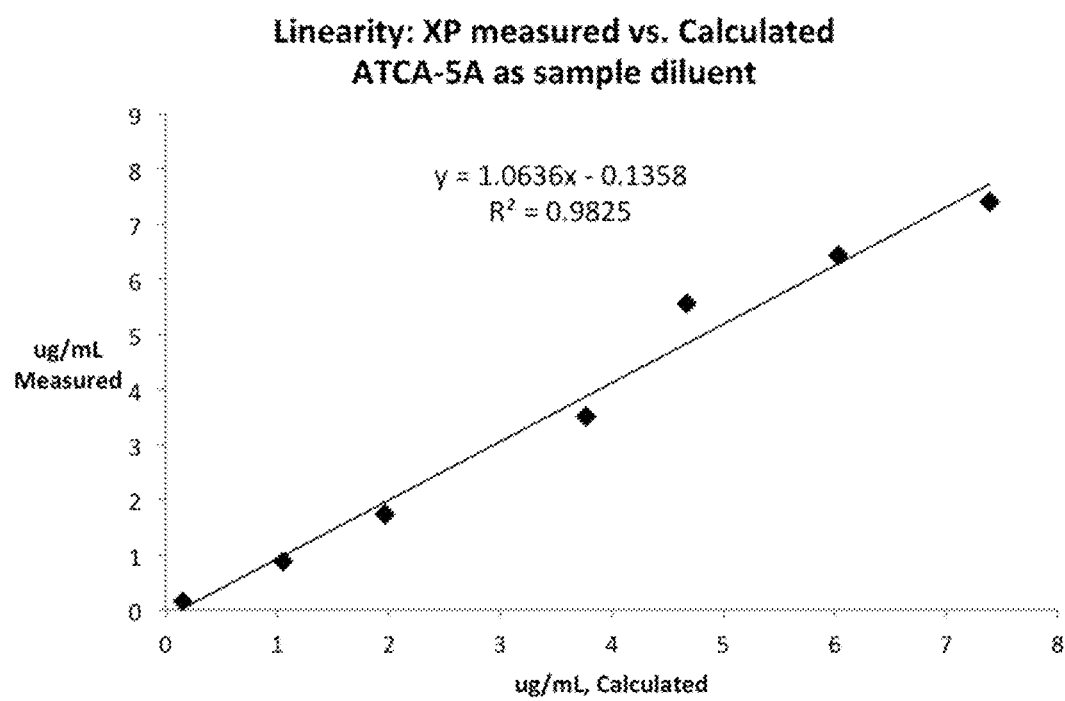
FIG. 8 illustrates a graph of a linear relationship between prototype CENTAUR® XP measured results to calculated results for samples diluted with acid treated, charcoal absorbed human serum in an example, according to an embodiment consistent with the principles described herein.

FIG. 8 shows a linearity plot of the prototype CENTAUR® XP measured doses versus calculated doses from Table 15.

TABLE 15

Sample Preparation of IGFBP-3 in ATCA-5A and Doses in µg/Ml

| ATCA-5A as a Diluent | Sample Prep | Calculated Dose | Measured Dose |
|---|---|---|---|
| P1 | P1 | 0.15 | 0.15 |
| P2 | P1 + P3 | 1.05 | 0.88 |
| P3 | P1 + P4 | 1.96 | 1.74 |
| P4 | P1 + P7 | 3.77 | 3.51 |
| P5 | P3 + P7 | 4.67 | 5.55 |
| P6 | P5 + P7 | 6.03 | 6.44 |
| P7 | P7 | 7.39 | 7.39 |

P7: the undiluted sample
P1: ACTA-5A

Thus, there have been described examples and embodiments of a human insulin-like growth factor (IGF) binding protein stock solution and a method of forming a concentrated IGF binding protein solution that both include a non-recombinant human insulin-like growth factor (IGF) binding protein 3 (nr-IGFBP-3), and a kit comprising a set of calibration standards that includes the nr-IGFBP-3 in different concentrations to encompass a range of concentrations of IGFBP-3 analyte in a human patient immunoassay. Moreover, there has been described examples and embodiments of a method of making a human serum diluent for the set of calibration standards that is substantially free of IGF binding proteins. It should be understood that the above-described examples and embodiments are merely illustrative of some of the many specific embodiments and examples that represent the principles described herein. Clearly, those skilled in the art can readily devise numerous other arrangements without departing from the scope as defined by the following claims.

What is claimed is:

1. A method of forming a concentrate of a non-recombinant human insulin-like growth factor (IGF) binding protein 3 (nr-IGFBP-3) in a native heterogeneous form in aqueous solution, the method comprising:
    (1) contacting a porous matrix with an aqueous solution, wherein the aqueous solution is human serum or IGF binding protein from the human serum; and
    (2) collecting concentrated nr-IGFBP-3 in the native heterogeneous form in aqueous solution from the porous matrix, the collected nr-IGFBP-3 in aqueous solution having a concentration within a range of from about 16 micrograms per milliliter (µg/ml) to about 40 µg/ml; and
    wherein the concentrate contains no recombinant IGFBP-3.

2. The method of claim 1, wherein the porous matrix is one or more of an ultrafiltration disc, a filtration membrane, and a sepharose-based resin.

3. The method of claim 1, further comprising the step of forming the aqueous solution of human serum of step (1) by mixing human serum with a first buffer solution, and wherein contacting the porous matrix with the aqueous solution comprises the steps of:
    applying the human serum in the first buffer solution to a chromatography column with a sepharose-based resin equilibrated with a second buffer solution to separate nr-IGFBP-3 from other serum proteins in the human serum;
    eluting the nr-IGFBP-3 from the sepharose-based resin with a third buffer solution; and
    applying the eluted nr-IGFBP-3 in the third buffer solution to a filtration membrane with an exchange buffer to buffer exchange and concentrate the nr-IGFBP-3 in aqueous solution.

4. The method of claim 1, further comprising the step of forming the aqueous solution of IGF binding protein from the human serum of step (1) comprising:
    mixing the human serum with a saturated anti-chaotropic salt solution to form a mixture;
    isolating the IGF binding protein from the mixture; and
    reconstituting the isolated IGF binding protein in a buffer solution; and
    wherein contacting the porous matrix with the aqueous solution comprises applying the reconstituted IGF binding protein in buffer solution to one or both of a filtration membrane and an ultrafiltration disc with an exchange buffer to buffer exchange and to concentrate nr-IGFBP-3 in aqueous solution.

5. The method of claim 4, wherein the saturated anti-chaotropic salt solution comprises an anti-chaotropic sulfate salt in water.

6. The method of claim 4, wherein the saturated anti-chaotropic salt solution comprises an ammonium sulfate salt in a sodium phosphate solution.

7. The method of claim 1, wherein the step of contacting the porous matrix with the aqueous solution comprises tangential flow filtration with a buffer exchange solution.

8. The method of claim 1, wherein the aqueous solution in which the nr-IGFBP-3 is disposed comprises a buffer selected from the group consisting of borate, phosphate, carbonate, Tris (Tris (hydroxymethyl) amino-methane), barbital, PIPES (piperazine-N,N-bis (2-ethanesulfonic acid)), HEPES (4-(2-hydroxyethyl)-1-piperazineethanesulfonic acid), MES (2-(N-morpholino)-ethanesulfonic acid), ACES (N-(2-Acetamido)-2-aminoethanesulfonic acid), MOPS (3-(N-morpholino) propanesulfonic acid), BICINE (N,N-bis (2-hydroxyethyl)-glycine), and any combination thereof.

9. The method of claim 1, wherein the aqueous solution has a pH in a range of from about 7.0 to about 9.0.

10. The method of claim 1, further comprising the step of preparing a set of calibrators from the concentrated nr-IGFBP-3 solution by diluting the concentrated nr-IGFBP-3 solution to various concentrations, wherein the concentration of nr-IGFBP-3 in each calibrator is different and is within a range of from about 0.5 µg/ml to about 16 µg/ml, the set of calibrators being configured to calibrate measurement of one or both of IGFBP-3 and IGF-1 in patient samples.

11. The method of claim 10, wherein the concentrated nr-IGFBP-3 solution is diluted with different quantities of an acid treated and charcoal absorbed human serum diluent that is substantially free of IGF binding protein.

12. The method of claim 1, further comprising the step of preparing a set of calibrators for an IGFBP-3 analyte immunoassay from the concentrated nr-IGFBP-3 solution by diluting the concentrated nr-IGFBP-3 solution to various concentrations in a human serum diluent, wherein the concentration of nr-IGFBP-3 in each calibrator is different and is within a range of from about 16 µg/ml to about 40 µg/ml, the set of calibrators being configured to calibrate measurement of one or both of IGFBP-3 and IGF-1 in patient samples.

13. The method of claim 12, wherein the human serum diluent is an acid treated and charcoal absorbed human serum diluent that is substantially free of IGF binding protein.

14. The method of claim 1, wherein the concentrated nr-IGFBP-3 in native heterogeneous form comprises glycosylated nr-IGFBP-3.

15. The method of claim 1, wherein the concentrated nr-IGFBP-3 in native heterogeneous form comprises at least one complex formed with at least one protein selected from the group consisting of insulin-like growth factor-1 (IGF-1), insulin-like growth factor-2 (IGF-2), acid-labile subunit protein (ALS), and combinations thereof.

16. The method of claim 1, wherein the concentrated nr-IGFBP-3 in native heterogeneous form has a nominal molecular weight in a range of from about 25 kDa to about 155 kDa.

17. A kit comprising a set of calibrators produced by the method of claim 10.

18. A kit comprising a set of calibrators produced by the method of claim 12.

19. A human insulin-like growth factor (IGF) binding protein stock calibration solution for automated immunoassay equipment prepared by the method of claim 1, wherein the calibration solution comprises:

a non-recombinant human IGF binding protein-3 (nr-IGFBP-3); and an aqueous buffered medium in which the nr-IGFBP-3 is disposed, the aqueous buffered medium comprising a buffer selected from the group consisting of borate, phosphate, carbonate, Tris (Tris (hydroxymethyl) amino-methane), barbital, PIPES (piperazine-N,N-bis (2-ethanesulfonic acid)), HEPES (He-4-(2-hydroxyethyl)-1-piperazineethanesulfonic acid), MES (2-(N-morpholino)-ethanesulfonic acid), ACES (N-(2-Acetamido)-2-aminoethanesulfonic acid), MOPS (3-(N-morpholino)propanesulfonic acid), BICINE (N,N-bis (2-hydroxyethyl)-glycine), and any combination thereof, wherein the aqueous buffered medium has a pH in a range of from about 7.0 to about 9.0; and wherein the calibration solution has an nr-IGFBP-3 concentration ranging from about 16 micrograms per milliliter (µg/ml) to about 40 µg/ml; and wherein the calibration solution contains no recombinant IGFBP-3.

20. The human IGF binding protein stock calibration solution of claim 19, wherein the nr-IGFBP-3 concentration is within a range of about 20 µg/ml to about 30 µg/ml, and wherein the aqueous buffered medium has a pH in a range of from about 7.25 to about 8.6.

21. The human IGF binding protein stock calibration solution of claim 19, wherein the aqueous buffered medium comprises at least one of phosphate buffered saline (PBS), PBS plus sodium azide, and Tris.

* * * * *